US012317795B2

(12) United States Patent
Nguyen et al.

(10) Patent No.: US 12,317,795 B2
(45) Date of Patent: Jun. 3, 2025

(54) CLUBROOT RESISTANT BRASSICA PLANTS

(71) Applicant: BASF Agricultural Solutions US LLC, Florham Park, NJ (US)

(72) Inventors: Thi Ninh Thuan Nguyen, Deinze (BE); Godfrey Chongo, Saskatoon (CA); Jasper Devlamynck, Deinze (BE); Geoffrey Wagner, Zwijnaarde (BE)

(73) Assignee: BASF Agricultural Solutions US LLC, Research Triangle Park, NC (US)

( * ) Notice: Subject to any disclaimer, the term of this patent is extended or adjusted under 35 U.S.C. 154(b) by 519 days.

(21) Appl. No.: 17/431,119

(22) PCT Filed: Feb. 14, 2020

(86) PCT No.: PCT/US2020/018249
§ 371 (c)(1),
(2) Date: Aug. 13, 2021

(87) PCT Pub. No.: WO2020/168166
PCT Pub. Date: Aug. 20, 2020

(65) Prior Publication Data
US 2022/0201954 A1 Jun. 30, 2022

(30) Foreign Application Priority Data
Feb. 15, 2019 (EP) ..................................... 19157382

(51) Int. Cl.
*A01H 6/20* (2018.01)
*A01H 1/00* (2006.01)
*A01H 5/06* (2018.01)

(52) U.S. Cl.
CPC ............. *A01H 1/1245* (2021.01); *A01H 5/06* (2013.01); *A01H 6/202* (2018.05)

(58) Field of Classification Search
CPC ....... A01H 6/204; A01H 6/202; A01H 1/1245
See application file for complete search history.

(56) References Cited

U.S. PATENT DOCUMENTS

| 5,689,041 | A | 11/1997 | Mariani et al. |
| 5,792,929 | A | 8/1998 | Mariani et al. |
| 2012/0204286 | A1 | 8/2012 | Gingera et al. |
| 2016/0249562 | A1 | 9/2016 | Patel et al. |
| 2018/0305774 | A1 | 10/2018 | Christianson et al. |

FOREIGN PATENT DOCUMENTS

| WO | 2012/039445 A1 | 3/2012 |
| WO | 2017102923 A1 | 6/2017 |

OTHER PUBLICATIONS

Werner et al., 2008, Genetic mapping of clubroot resistance genes in oilseed rape. Theoretical and applied genetics, 116, 363-372. (Year: 2008).*
Karim et al., 2016, Marker-assisted selection of low erucic acid quantity in short duration *Brassica rapa*. Euphytica, 208, 535-544. (Year: 2016).*
Hatakeyama et al., 2013, Identification and characterization of Crr1a, a gene for resistance to clubroot disease (*Plasmodiophora brassicae* Woronin) in *Brassica rapa* L. PloS one, 8(1), e54745. (Year: 2013).*
Zhan et al., 2015, Development of close linked marker to PbBa8. 1 conferring canola resistance to Plasmodiophora brassicae. Chin. J. Oil Crop Sci. 6, 766-771. (Original) (Year: 2015).*
Zhan et al., 2015, Development of close linked marker to PbBa8. 1 conferring canola resistance to Plasmodiophora brassicae. Chin. J. Oil Crop Sci. 6, 766-771. (English translated version). (Year: 2015).*
Karim et al., 2016, Marker-assisted selection of low erucic acid quantity in short duration *Brassica rapa*. Euphytica, 208, 535-544 (reference send while restriction/election LOU). (Year: 2016).*
Li et al., 2012, Effect of phosphorus fertilization on yield and phosphorus use efficiency of winter oilseed rape (*Brassica napus* L.) with two different cropping intensities in the middle and lower reaches of Yangtze River. Journal of Food, Agriculture and Environment, 10(2), 576-579. (Year: 2012).*
Rahman et al., 2011, Breeding for clubroot resistant spring canola (*Brassica napus* L.) for the Canadian prairies: Can the European winter canola cv. Mendel be used as a source of resistance ?. Canadian Journal of Plant Science, 91(3), 447-458. (Year: 2011).*
Hadi et al., 2012, Glyphosate tolerance in transgenic canola by a modified glyphosate oxidoreductase (gox) gene. Progress in Biological Sciences, 2(1), 50-58. (Year: 2012).*
Seo et al. (Year: 2016, Journal: Plant Mol. Biol., vol. 90, pp. 503-516) (Year: 2016).*
Park et al. (Year Published: 2017, Journal: Hortic. Enciron. Biotechnol., vol. 58(1), pp. 48-55). (Year: 2017).*
NCBI GenBank: CM017929.*Brassica rapa* subsp. pekinensis cultivar CT001 chromosome A8, whole genome shotgun sequence. Sep. 20, 2019. (Year: 2019).*
NCBI GenBank: LR031575. *Brassica rapa* genome, scaffold: A08. Nov. 16, 2018. (Year: 2018).*
Mauricio, 2001, Mapping Quantitative Trait Loci in Plants: Uses and Caveats for Evolutionary Biology, Nature Reviews Genetics 2:370-381. (Year: 2001).*
Werner, et al. "Genetic mapping of clubroot resistance genes in oilseed rape." Theor Appl gent. Feb. 2008, vol. 116, No. 3, pp. 363-372.
Wu et al. "Zero erucic acid trait of rapeseed (*Brassica napus* L.) results from a deletion of four base pairs in the fatty acid elongase 1 gene." Theor Appl Genet. Feb. 2008, vol. 116, No. 4, pp. 491-499.

(Continued)

*Primary Examiner* — David H Kruse
*Assistant Examiner* — Santosh Sharma
(74) *Attorney, Agent, or Firm* — ArentFox Schiff LLP

(57) ABSTRACT

The invention provides low erucic, clubroot resistant *Brassica* plants, plant material and seeds, characterized in that these products harbor a specific CrS clubroot resistance locus in their genome. Tools are also provided which allow detection of the CrS clubroot resistance locus.

14 Claims, 6 Drawing Sheets

Specification includes a Sequence Listing.

(56) References Cited

OTHER PUBLICATIONS

International Search Report for PCT Patent Application No. PCT/EP2018/018249, Issued on Jul. 30, 2020, 3 pages.
European Search Report for EP Patent Application No. 20755893.3, Issued on Nov. 10, 2022, 3 pages.
Hirani, et al., "Transferring clubroot resistance from Chinese cabbage (*Brassica rapa*) to canola (*B. napus*)", Canadian Journal of Plant Pathology, vol. 38, Issue 1, Mar. 24, 2016, pp. 82-90.
Rahman, et al., "Breeding for clubroot resistant spring canola (*Brassica napus* L.) for the Canadian prairies: Can the European winter canola cv. Mendel be used as a source of resistance?", Canadian Journal of Plant Science, vol. 91, Issue 3, Jan. 1, 2011, pp. 447-458.
"*Brassica napus* cultivar Ningyou7 chromosome A8 fatty acid elongase (FAE1) gene, complete cds", GenBank, Database accession No. EU543282.1, Nov. 12, 2008, 2 pages.
Bayer, et al., "Assembly and comparison of two closely related *Brassica napus* genomes", Plant Biotechnology Journal, vol. 15, Issue 12, Apr. 12, 2017, pp. 1602-1610.
Bortesi, et al., "Patterns of CRISPR/Cas9 activity in plants, animals and microbes", Plant Biotechnology Journal, vol. 14, Issue 12, Sep. 10, 2016, pp. 2203-2216.
Burstein, et al., "New CRISPR-Cas systems from uncultivated microbes", Nature, vol. 542, Issue 7640, Dec. 22, 2016, pp. 237-241.
Chen, et al., "Identification of Novel QTLs for Isolate-Specific Partial Resistance to Plasmodiophora brassicae in *Brassica rapa*", PLoS One, vol. 8, Issue 12, Dec. 20, 2013, pp. 1-11.
Diederichsen, et al., "Status and Perspectives of Clubroot Resistance Breeding in Crucifer Crops", Journal of Plant Growth Regulation, vol. 28, Issue 3, May 8, 2009, pp. 265-281.
F. M. Humpherson-Jones, "Glasshouse evaluation of fungicides, biocides and surfactants for control of clubroot", Sup tests of Agrochemicals and Cultivars, vol. 114, 1989, pp. 36-37.
Geoffrey R. Dixon, "The Occurrence and Economic Impact of Plasmodiophora brassicae and Clubroot Disease", Journal of Plant Growth Regulation, vol. 28, Issue 3, Apr. 22, 2009, pp. 194-202.
Hatakeyama, et al., "Identification and Characterization of Crr1a, a Gene for Resistance to Clubroot Disease (Plasmodiophora brassicae Woronin) in *Brassica rapa* L.", Plos One, vol. 8, Issue 1, Jan. 30, 2013, pp. 1-10.
Horiuchi, et al., "A simple greenhouse technique for obtaining high level of clubroot incidence", Chugoku National Agricultural Experiment Station- Series E. Environment Division, Issue 17, Mar. 1980, pp. 33-55.
Hwang, et al., "Plasmodiophora brassicae: a review of an emerging pathogen of the Canadian canola (Brassica hapus) crop", Molecular Plant Pathology, vol. 13, Issue 2, Jun. 1, 2011, pp. 105-113.
International Search Report for PCT Patent Application No. PCT/US2020/018249, Issued on Jul. 30, 2020, 4 pages.
Kato, et al., "Fine mapping of the clubroot resistance gene CRb and development of a useful selectable marker in *Brassica rapa*", Breeding Science, vol. 63, Issue 1, 2013, pp. 116-124.
Komor, et al., "Programmable editing of a target base in genomic DNA without double-stranded DNA cleavage", Nature, vol. 533, Issue 7603, Apr. 20, 2016, pp. 420-424.
Kuginuki, et al., "Variation in Virulence of Plasmodiophora brassicae in Japan Tested with Clubroot-resistant Cultivars of Chinese Cabbage (*Brassica rapa* L. ssp. *pekinensis*)", European Journal of Plant Pathology, vol. 105, Issue 4, Jun. 1999, pp. 327-332.
Ma, et al., "CRISPR/Cas9 Platforms for Genome Editing in Plants: Developments and Applications", Molecular Plant, vol. 9, Issue 7, Jul. 6, 2016, pp. 961-974.
Murovec, et al., "New variants of CRISPR RNA-guided genome editing enzymes", Plant Biotechnology Journal, vol. 15, Issue 8, Apr. 1, 2017, pp. 917-926.
Nakade, et al., "Cas9, Cpf1 and C2c1/2/3—What's next?", Bioengineered, vol. 8, Issue 3, Apr. 6, 2017, pp. 265-273.
Neik, et al., "Current status and challenges in identifying disease resistance genes in *Brassica napus*", Frontiers in Plant Science, vol. 8, Article No. 1788, Nov. 6, 2017, pp. 1-37.
Osakabe, et al., "Genome Editing with Engineered Nucleases in Plants", Plant and Cell Physiology, vol. 56, Issue 3, Nov. 20, 2014, pp. 389-400.
P. H. Williams, "A system for the determination of races of Plasmodiophora brassicae that infect Cabbage and Rutabaga.", Phytopathology, vol. 56, Issue 6, 1966, pp. 624-626.
Pang, et al., "Genetic detection of clubroot resistance loci in a new population of *Brassica rapa*", Horticulture, Environment, and Biotechnology, vol. 55, Issue 6, Jan. 15, 2015, pp. 540-547.
Piao, et al., "Genetics of Clubroot Resistance in *Brassica* Species", Journal of Plant Growth Regulation, vol. 28, Issue 3, Apr. 16, 2009, pp. 252-264.
Some, et al., "Variation for virulence on *Brassica napus* L. amongst Plasmodiophora brassicae collections from France and derived single-spore isolates", Plant Pathology, vol. 45, Issue 3, Jun. 1996, pp. 432-439.
Strelkov, et al., "Characterization of Plasmodiophora brassicae populations from Alberta, Canada", Canadian Journal of Plant Pathology, vol. 28, Issue 3, 2006, pp. 467-474.
Strelkov, et al., "The occurrence and spread of club-root on Canola in Alberta in 2018", Canadian Plant Disease Survey 2019 vol. 99: Disease Highlights 2018, Canadian Journal of Plant Pathology, vol. 41, Sup 1, Aug. 2, 2019, pp. 129-131.
Strelkov, et al., "Virulence and pathotype classification of Plasmodiophora brassicae populations collected from clubroot resistant canola (*Brassica napus*) in Canada", Canadian Journal of Plant Pathology, vol. 40, Issue 2, May 11, 2018, pp. 284-298.
Jeno, et al., "Molecular characterization of the CRa gene conferring clubroot resistance in *Brassica rapa*", Plant Molecular Biology, vol. 80, Issue 6, Oct. 4, 2012, pp. 621-629.
Werner, et al., "Genetic mapping of clubroot resistance genes in oilseed rape", Theoretical and Applied Genetics, vol. 116, Issue 3, Article No. 363, Nov. 27, 2007, pp. 363-372.
Wu, et al., "Zero erucic acid trait of rapeseed (*Brassica napus* L.) results from a deletion of four base pairs in the fatty acid elongase 1 gene", Theoretical and Applied Genetics, vol. 116, Issue 4, Dec. 13, 2007, pp. 491-499.
Xue, et al., "Isolation and Variation in Virulence of Single-Spore Isolates of Plasmodiophora brassicae from Canada", Plant Disease, vol. 92, Issue 3, Feb. 12, 2008, pp. 456-462.
Yu, et al., "Genotyping-by-sequencing reveals three QTL for clubroot resistance to six pathotypes of Plasmodiophora prassicae in *Brassica rapa*", Scientific Reports, vol. 7, Issue 1, Article No. 4516, Jul. 3, 2017, pp. 1-11.
Zhang, et al., "Fine genetic and physical mapping of the CRb gene conferring resistance to clubroot disease in *Brassica rapa*", Molecular Breeding, vol. 34, Issue 3, May 17, 2014, pp. 1173-1183.

* cited by examiner

CLUBROOT RESISTANT BRASSICA PLANTS

CROSS-REFERENCE TO RELATED APPLICATIONS

This application is a National Stage Entry of PCT/US2020/018249, filed Feb. 14, 2020, which claims priority to EP application Ser. No. 19/157,382.3, filed Feb. 15, 2019, the disclosure of which are hereby incorporated by reference in their entirety.

FIELD OF THE INVENTION

The invention relates to the field of disease control in Brassica. Provided are Brassica plants comprising a clubroot resistance gene in their genome, and in particular Brassica plants with low levels of erucic acid. Also provided are methods and means to produce such plants and to detect a clubroot resistance gene.

BACKGROUND OF THE INVENTION

Clubroot is a disease caused by *Plasmodiophora brassicae* which affects the Brassicaceae family of plants, including many important vegetable and broad acre crops. All members of the family Brassicaceae are thought to be potential hosts for *Plasmodiophora brassicae* (Dixon, 2009, J Plant Growth Regul 28: 194). Susceptible cultivated crops include all varieties of *B. oleracea*, the Occidental cole vegetables (Brussels sprout, cabbages, calabrese/green broccoli, cauliflower, culinary and fodder kale, kohlrabi); *B. rapa* (syn. *B. campestris*) including turnip, turnip rape, sarson, and the enormous range of Oriental variants which provide leaf and root vegetables such as *Brassica rapa* var. *pekinensis* and *B. rapa* var. *chinensis* (Chinese cabbages); *B. napus* including swede (rutabaga), oilseed rape, and fodder rape; and seed, condiment (mustard), and vegetable crops derived from *B. carinata, B. nigra,* and *B. juncea.* Related genera such as radish (*Raphanus*), cruciferous weeds, for example, *Sinapis*, and decorative ornamentals including stocks (*Matthiola* spp) and wallflower (*Cheiranthus cheiri*) can be infected. The scientific model plant *Arabidopsis* is also a host of the pathogen (Dixon, 2009, supra).

Clubroot disease symptom development is characterized by the formation of club-shaped galls on the roots of affected plants. As a result, the nutrient and water uptake by infected roots is inhibited. Above-ground symptoms include wilting, stunting, yellowing and premature senescence (Hwang et al, 2012, Mol Plant Pathol 13: 105).

Clubroot disease is estimated to be present in approximately 10% of all areas where host plants are cultivated (Diederichsen et al, 2009, J Plant Growth Regul 28: 265). Clubroot has been largely a disease of vegetable crops in the last century. However, in 2003, 12 clubroot-infested commercial canola fields were found in the central part of the province of Alberta. Thereafter, the number of fields with confirmed clubroot infestations has increased steadily, and, by 2019, more than 3353 fields (over 35 000 ha) in Alberta, 51 in Saskatchewan and 35 in Manitoba had been identified as being infested with *P. brassicae* (Strelkov et al, 2019, Canadian Journal of Plant Pathology 41: supl: 129). Yield losses of 80%-91% were reported in studies with canola grown on clubroot-infested fields in Quebec. Seed quality was also reduced significantly, with declines of 4.7%-6.1% in oil content and 13%-26% in 1000-seed weights (Hwang et al., 2012, supra).

Plant resistance is a powerful tool to combat clubroot disease. Recently released resistant cultivars belong to three Brassica species: *B. napus, B. oleracea,* and *B. rapa* (Diederichsen et al., 2009, supra).

Resistant sources of the European fodder turnips (*B. rapa* ssp. *rapifera*) have been identified such as 'Gelria R', 'Siloga', 'Debra' and 'Milan White', which have been used to transfer the clubroot resistance genes to Chinese cabbage (Piao et al., 2009, J Plant Growth Regul 28: 252). Many race-specific, single and dominant R genes are indeed present in *B. rapa* (reviewed in Neik et al., 2017, Frontiers in Plant Science 8:1788). Crr2, CRc and Crr4 are mapped to chromosomes A01, A02 and A06, respectively. Several major genes were identified on chromosome A03: CRa, Crr3, CRb, CRb$^{Kato}$ and CRk. Different major genes or QTL have been mapped on chromosome A08: PbBa8.1 from ssp. *rapifera* ECD04 (Chen et al 2013 PLoS ONE 8(12): e85307), QS_B8.1 from 'Siloga' (Pang et al., (2014) Hort Environ Biotechnol 55:540-547), Rcr9 from 'Pluto' (Yu et al, 2017, Scientific Reports 7:4516), Crr1a and Crr1b (Hatakeyama et al., 2013, PLOS one 8: e54745).

In *B. oleracea*, completely resistant accessions have been rarely identified. The inheritance of the clubroot resistance in *B. oleracea* appears polygenic. (Piao et al., 2009, supra). At least 22 QTLs have been found in *B. oleracea*, indicating a complex genetic basis of clubroot resistance in *B. oleracea*. As the different mapping studies used different clubroot resistance sources and different *P. brassicae* isolates, a comparison of these QTLs is not possible (Piao et al., 2009, supra).

Clubroot resistance has also been observed in several *B. napus* cultivars. At least 22 QTLs for clubroot resistance have been identified in *B. napus*. A major gene, Pb-Bnl, has been mapped onto linkage group DY4, and at least two additive QTLs have been identified on chromosomes DY4 and DY15, respectively. In addition, epistatic interactions between nine regions with or without additive effects have been located. A major gene and two recessive genes derived from ECD04 have been identified in double-haploid populations. In resynthesized *B. napus* developed by crossing cv. Bohmerwaldkohl (*B. oleracea*) and ECD-04 (*B. rapa*), nineteen QTLs expressing resistance to seven isolated were detected on eight chromosomes, four of which were closely linked to each other on chromosome NO3, and three were linked on chromosome N08. Genes CRk and Crr3 are located in the similar region of PbBn-k-2, PbBn-1-1 , and PbBn-01:60-1 on NO3. CRa and CRb are independent from them. PbBn-01.07-2, PbBn-l-2, and PbBn-a-1 are linked to BRMS088 on chromosome N08 in *B. napus*, which is also linked with Crr1 on R8 in *B. rapa*. PbBn-k-1 is located on chromosome NO2. The QTLs located on NO3 and N19 contribute strong effects and confer broad-spectrum resistance (Piao et al., 2009, supra; and Werner et al., 2008, Theor Appl Genet 116:363; Neik et al., 2017, Frontiers in Plant Science 8:1788).

Until now, two clubroot resistance genes have been cloned: CRa and Crr1a. The CRa gene of *Brassica rapa* has been fine-mapped and a TIR-NBS-LRR gene has been identified as the CRa gene (Ueno et al., 2012, Plant Mol Biol 80: 621). The Crr1a gene has been mapped and isolated from the *B. rapa* European fodder turnip "Siloga". Crr1a also encodes a TIR-NB-LRR disease resistance protein (Hatakeyama et al., 2013, supra and WO2012/039445).

The CRb gene from *B. rapa* has been fine-mapped to a 140 kb genomic region. In this region, in which fourteen functional proteins were predicted, amongst which Rho family proteins and two TIR-NBS-LRR proteins, which could be candidate genes for CRb (Kato et al., 2013, Breeding Science 63: 116). This fine mapped CRb gene was renamed CRb$^{Kato}$ as its position on the genome does not match with the earlier mapped CRb gene (Zhang et al. 2014, Molecular Breeding 34: 1173).

To increase the durability of cultivar resistance, the combination of the different clubroot resistance genes into a single line will be an important means for breeding cultivars with resistance to a broader spectrum of physiological races. Therefore, in order to stack genes without linkage drag using marker-assisted selection and transgenic approaches, there remains a need to develop molecular markers linked to the clubroot resistance genes. This invention provides a clubroot resistance locus, as herein after described in the different embodiments, examples and claims.

Summary of the Preferred Embodiments of the Invention

In a first embodiment of the invention, a *Brassica* plant is provided comprising <2% erucic acid in the seed oil, and comprising a CrS clubroot resistance locus in a chromosomal segment comprising the marker M4. In another embodiment, said CrS clubroot resistance locus is in a chromosomal segment comprising the marker interval from marker M4 to M5. In another embodiment, said CrS clubroot resistance locus is in a chromosomal segment comprising the marker interval from marker M4 to M8, whereas in a further embodiment said CrS clubroot resistance locus is in a chromosomal segment comprising the marker interval from marker M4 to M11. In yet another embodiment, the plant according to the invention comprises the marker allele M4/R, whereas in yet another embodiment the plant according to the invention comprises the marker alleles M4/R and M5/R, or comprises the marker alleles M4/R, M5/R, M6/R and M7/R.

In another embodiment, the *Brassica* plant according to the invention does not comprise the marker allele M3/R, or M2/R, or M1/R, or a combination thereof.

In yet another embodiment, the *Brassica* plant according to the invention is a *Brassica napus* or a *Brassica rapa* plant, whereas in yet another embodiment, the *Brassica* plant according to the invention is a *Brassica napus* WOSR plant or a *Brassica napus* SOSR plant.

In another aspect the *Brassica* plant according to the invention is a Brassica napus WOSR plant wherein said chromosomal segment comprises the marker interval from marker M4 to M7. In yet another aspect the *Brassica* plant according to the invention is a *Brassica napus* SOSR plant wherein said chromosomal segment comprises the marker interval from marker M4 to M5, such as a *Brassica napus* SOSR plant comprising the marker interval from marker M4 to M8, such as a *Brassica napus* SOSR plant wherein said chromosomal segment is obtainable from reference seeds deposited at NCIMB under accession number NCIMB 43341.

In another aspect, the *Brassica* plant according to the invention is resistant to *P. brassicae* pathotypes P2, P3, P5, P6 or P8 or to isolate CR11.

In yet another aspect, the *Brassica* plant according to the invention is heterozygous for said clubroot resistance locus, whereas in another aspect, the *Brassica* plant according to the invention is homozygous for said clubroot resistance locus.

Yet another embodiment provides the *Brassica* plant according to the invention which further comprises a gene conferring herbicide tolerance. In another embodiment, the gene conferring herbicide tolerance tolerance is a gene which confers resistance to glufosinate or to glufosinate ammonium or a gene conferring resistance to glyphosate.

Seeds of the plants according to the invention are also provided.

Another aspect of the invention provides a method for producing a clubroot resistant *Brassica* plant, said method comprising (a) identifying at least one *Brassica* plant comprising a CrS clubroot resistance locus with at least one marker within 10 cM of the marker interval from M4 to M5, and, and (b) selecting a plant comprising said CrS clubroot resistance locus. In a further embodiment, said method comprising identifying at least one *Brassica* plant comprising at least one marker in the marker interval from M4 to M11, and not comprising the marker allele M3/R or not comprising marker allele M2/R, or not comprising marker allele M1/R, whereas in another embodiment, said *Brassica* plant is identified using markers in the marker interval from M4 to M5.

Another embodiment of the invention provides a method for producing a clubroot resistant *Brassica* plant, said method comprising (a) crossing a first *Brassica* plant comprising a CrS clubroot resistance locus with a second plant; and (b) identifying a progeny plant comprising at least one marker within 10 cM of the marker interval from M4 to M5. In a further embodiment, said method comprises identifying a progeny plant comprising at least one marker in the marker interval from M4 to M11, and not comprising the marker allele M3/R or not comprising marker allele M2/R, or not comprising marker allele M1/R.

In another embodiment, a method is provided for producing a clubroot resistant *Brassica* plant comprising introducing the CrS clubroot resistance locus into a plant not comprising the CrS clubroot resistance locus using genome editing.

It is another object of the invention to provide the use of at least one marker within 10 cM of the marker interval from M4 to M5 to identify a plant comprising the CrS clubroot resistance locus. It is another object of the invention to provide the use of markers M4, M5, M6, M7, M8, M9, M10 and/or M11 to identify a plant comprising the CrS clubroot resistance locus.

In yet another aspect, a method is provided for the protection of a group of cultivated plants according to the invention in a field wherein weeds are controlled by the application of a composition comprising one or more herbicidal active ingredients. In a further aspect, said plants comprise a gene which confers resistance to glufosinate or to glufosinate ammonium or a gene conferring resistance to glyphosate, and the herbicide is glufosinate or glufosinate ammonium or glyphosate.

GENERAL DEFINITIONS

Figure 1:
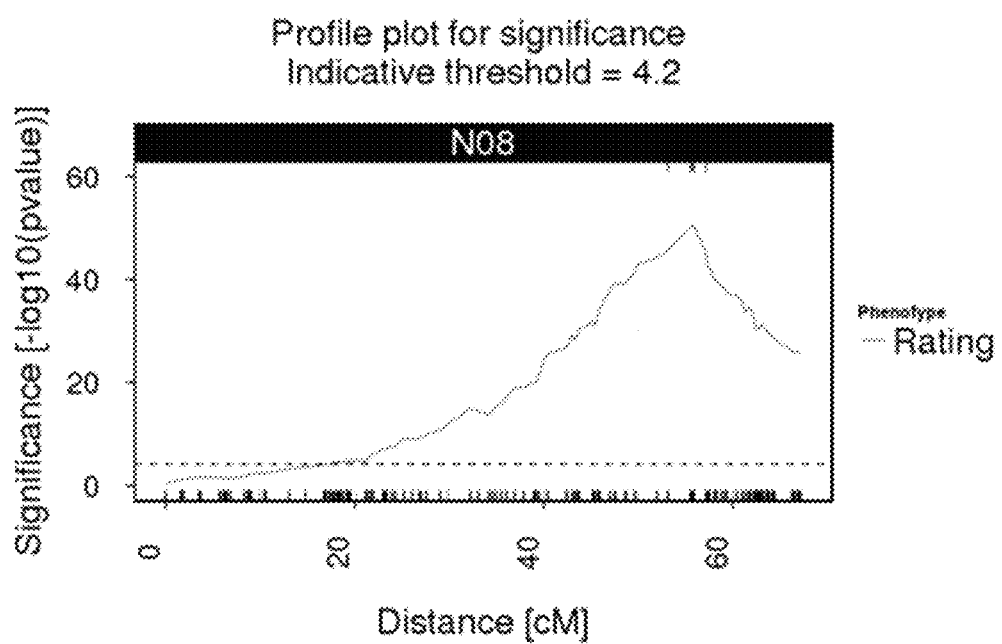
FIG. 1. Mapping of CrS clubroot resistance locus.

A "clubroot resistance gene" as used herein refers to a DNA sequence which confers, or is associated with, enhanced resistance of a plant, such as a *Brassicaceae* plant, such as a *Brassica* plant, to *Plasmodiophora brassicae*, compared to a plant lacking the resistance gene(s) or having a non-functional (or inactivated) form of the gene(s).

"Clubroot" as used herein refers to the disease caused by the pathogen *Plasmodiophora brassicae*.

"Clubroot resistance" as used herein refers to resistance to one or more Plasmodiophora brassicae isolates, such as, but not limited to, resistance to the *Plasmodiophora brassicae* pathotypes P2, P3, P5, P6 and/or P8 as classified by Williams (1966) Phytopathology, 56, 624-626, and/or to isolate CR11, and/or to isolates including 2B, 3A, 5X, and 8P based on the Canadian Clubroot Differential set (CCD) of Strelkov et al. 2018, Can J Plant Pathology pp 284. Said resistance refers to a reduction in damage caused by clubroot infection compared to damage caused on control plants. Damage can be assessed as, for example, formation of club-shaped galls on the roots, occurrence of wilting, stunting, yellowing, premature senescence etc. In particular, a reduction in damage is manifested in a reduced yield loss when plants are grown under disease pressure in the field, compared to control plants. Such reduction in yield loss can, for example, be due to the fact that the infection, reproduction, spread or survival of the pathogen is reduced or prevented in plants with enhanced resistance. Said resistance may also refer to plants that are completely resistant, i.e., plants on which no disease symptoms are found.

Clubroot resistance can be assessed using a scale from zero to three: zero: no clubbing, one: <25% of root system clubbed; two: 25 to 50% of root system clubbed; three: >50% of root system clubbed (Humpherson-Jones, 1989, Tests Agro Cult 10:36). The Index of Disease (ID) can be calculated using the following equation:

$$[(\# \text{ plants in class } 0*0) + ([(\# \text{ plants in class } 1*1) + (\# \text{ plants in class } 2*2) + (\# \text{ plants in class } 3*3)] / \text{total number of plants} * 3$$

(Strelkov et al., 2006, Can J Plant Pathol 28:467).

It is understood that environmental conditions, such as location, weather conditions and disease pressure, as well as individual perception of the person assessing disease symptoms, can have an effect on the scoring of clubroot resistance. Hence, variation in these factors in comparative tests should be minimized. Any other resistance ratings known in the art can be applied in accordance with this invention to compare the plants of the invention with control plants.

A plant which is clubroot resistant refers to a plant assessed at scale zero or one upon natural or artificial infection with the clubroot pathogen. A clubroot resistant population is a population with a disease index (ID) of less than 30%. A plant with increased clubroot resistance is a plant in which the percentage of the root system which is clubbed is decreased with at least 5%, or at least 10%, or at least 15%, or at least 20%, or at least 30%, or at least 40%, or at least 50%, or at least 70%, or at least 95%, or with 100%, i.e. no clubbing, or refers to a population of plants in which the disease index is reduced with at least 3%, or at least 5%, or at least 8%, or at least 10%, or at least 15%, or at least 20%, or at least 30%, or at least 40%, or at least 50%, or at least 70%, or at least 95%, or with 100%, i.e. all plants of the population are classified in class 0 (no clubbing).

A "CrS clubroot resistance locus", or "CrS resistance locus", or "CrS locus", as used herein, is a locus that confers resistance to *Plasmodiophora brassicae* pathotypes P2, P3, P5, P6 and/or P8 as classified by Williams (1966) Phytopathology, 56, 624-626, and/or to isolate CR11. The CrS clubroot resistance locus refers to a position on the chromosome. This position can be identified by the location on the genetic map of a chromosome, or by the location on the physical position of a chromosome, e.g. when the genome sequence is available.

A "locus" (plural loci) as used herein is the position that a gene occupies on a chromosome. A "clubroot resistance locus" refers to the position on the chromosome where a clubroot resistance gene is located. This position can be identified by the location on the genetic map of a chromosome. Included in this definition is the fragment (or segment) of genomic DNA of the chromosome on which the clubroot resistance locus is located. Said clubroot resistance locus can be the CrS clubroot resistance locus or another clubroot resistance locus. A locus which does not comprise the CrS clubroot resistance gene according to the invention, which is at the position on the chromosome corresponding to the position where the CrS clubroot resistance gene is located in a resistant line, can be referred to as "CrS clubroot susceptibility locus". A QTL (quantitative trait locus), as used herein, and refers to a position on the genome that corresponds to a measurable characteristic, i.e. a trait, such as the presently described CrS locus.

As used herein, the term "allele(s)" of a gene means any of one or more alternative forms of a gene at a particular locus. In a diploid cell of an organism, alleles of a given gene are located at a specific location or locus (loci plural) on a chromosome. One allele is present on each chromosome of the pair of homologous chromosomes or possibly on homeologous chromosomes.

As used herein, the term "homologous chromosomes" means chromosomes that contain information for the same biological features and contain the same genes at the same loci but possibly different alleles of those genes. Homologous chromosomes are chromosomes that pair during meiosis. "Non-homologous chromosomes", representing all the biological features of an organism, form a set, and the number of sets in a cell is called ploidy. Diploid organisms contain two sets of non-homologous chromosomes, wherein each homologous chromosome is inherited from a different parent. In tetraploid species, two sets of diploid genomes exist, whereby the chromosomes of the two genomes are referred to as "homeologous chromosomes" (and similarly, the loci or genes of the two genomes are referred to as homeologous loci or genes). Likewise, tetraploid species have two sets of diploid genomes, etc. A diploid, tetraploid or hexaploid plant species may comprise a large number of different alleles at a particular locus. The ploidy levels of *Brassica* species are diploid (*Brassica rapa*, AA; *Brassica nigra* BB; *Brassica oleracea*, CC), and tetraploid (*Brassica juncea*, AABB; *Brassica napus*, AACC; *Brassica carinata*, BBCC).

As used herein, the term "heterozygous" means a genetic condition existing when two different alleles reside at a specific locus, but are positioned individually on corresponding pairs of homologous chromosomes in the cell. Conversely, as used herein, the term "homozygous" means a genetic condition existing when two identical alleles reside at a specific locus, but are positioned individually on corresponding pairs of homologous chromosomes in the cell.

An allele of a particular gene or locus can have a particular penetrance, i.e. it can be dominant, partially dominant, co-dominant, partially recessive or recessive. A dominant allele is a variant of a particular locus or gene that when present in heterozygous form in an organism results in the same phenotype as when present in homozygous form. A recessive allele on the other hand is a variant of an allele that in heterozygous form is overruled by the dominant allele thus resulting in the phenotype conferred by the dominant allele, while only in homozygous form leads to the recessive phenotype. Partially dominant, co-dominant or partially recessive refers to the situation where the heterozygote displays a phenotype that is an intermediate between the phenotype of an organism homozygous for the one allele and an organism homozygous for the other allele of a particular locus or gene. This intermediate phenotype is a demonstration of partial or incomplete dominance or penetrance. When partial dominance occurs, a range of phenotypes is usually observed among the offspring. The same applies to partially recessive alleles.

As used herein, the term "chromosome interval" is a contiguous linear span of genomic DNA on a single chromosome. The "chromosome interval" can be defined by the genetic map and can be determined based on the genetic positions of markers. The "chromosome interval" can also be defined based on a physical structure of the chromosome, e.g. by the genome sequence.

The term "marker interval" refers to a chromosome interval defined by markers. The marker interval from a first to a second marker is the chromosome interval from said first to said second marker, including said markers. The marker interval between a first and a second marker is the chromosome interval between said first and said second marker. The marker interval can be defined by the genetic map and can be based on the genetic position of the markers. The marker interval can also be defined based on a physical structure of the chromosome, e.g. as based on the genome sequence.

The position of the chromosomal segments identified, and the markers thereof, when expressed as recombination frequencies or map units, are provided herein as a matter of general information. The embodiments described herein were obtained using particular Brassica populations. Accordingly, the positions of particular segments and markers as map units are expressed with reference to the used populations. It is expected that numbers given for particular segments and markers as map units may vary from cultivar to cultivar and are not part of the essential definition of the DNA segments and markers, which DNA segments and markers are otherwise described, for example, by nucleotide sequence.

As used herein, a "genetic map" or "linkage map" is a table for a species or experimental population that shows the position of its genetic markers relative to each other in terms of recombination frequency. A linkage map is a map based on the frequencies of recombination between markers during crossover of homologous chromosomes.

A "physical map" of the genome refers to absolute distances (for example, measured in base pairs), such as distances based on a genome sequence. The position of markers on a physical map can, for example, be determined by blasting the sequence of the markers against the genome sequence.

The terms "genetically linked", "linked", "linked to" or "linkage", as used herein, refers to a measurable probability that genes or markers located on a given chromosome are being passed on together to individuals in the next generation. Thus, the term "linked" may refer to one or more genes or markers that are passed together with a gene with a probability greater than 0.5 (which is expected from independent assortment where markers/genes are located on different chromosomes). Because the proximity of two genes or markers on a chromosome is directly related to the probability that the genes or markers will be passed together to individuals in the next generation, the term genetically linked may also refer herein to one or more genes or markers that are located within about 50 centimorgan (cM) or less of one another on the same chromosome. Genetic linkage is usually expressed in terms of cM. Centimorgan is a unit of recombinant frequency for measuring genetic linkage, defined as that distance between genes or markers for which one product of meiosis in 100 is recombinant, or in other words, the centimorgan is equal to a 1% chance that a marker at one genetic locus on a chromosome will be separated from a marker at a second locus due to crossing over in a single generation. It is often used to infer distance along a chromosome. The number of base-pairs to which cM correspond varies widely across the genome (different regions of a chromosome have different propensities towards crossover) and the species (i.e. the total size of the genome). Thus, in this respect, the term linked can be a separation of about 50 cM, or less such as about 40 cM, about 30 cM, about 20 cM, about 10 cM, about 7.5 cM, about 6 cM, about 5 cM, about 4 cM, about 3 cM, about 2.5 cM, about 2 cM, or even less. Particular examples of markers linked to the CrS clubroot resistance locus are specified in Table 8.

"Upstream" of a certain position on a genome reference sequence refers to the 5' direction. With reference to the genome reference sequence, the upstream direction refers to a lower number of said position. "Upstream" of a certain position on a genome means in the direction to a lower number on the genetic map.

"Downstream" of a certain position on a genome reference sequence refers to the 3' direction. With reference to the genome reference sequence, the upstream direction refers to a higher number of said position. "Downstream" of a certain position on a genome means the direction to a higher number on the genetic map.

"Left" or "at the left side" of a certain position on the genetic map refers to the direction of the lower number of the genetic position (in cM). For example, the "left flanking marker" is the marker in a QTL interval with the lowest number in the population position. The "left side" of a marker is a position on the genetic map with a lower number (in cM).

"Right" or "at the right side" of a certain position on the genetic map refers to the direction of the higher number of the genetic position (in cM). For example, the "right flanking marker" is the marker in a QTL interval with the highest number in the population position. The "right side" of a marker is a position on the genetic map with a higher number (in cM).

"Backcrossing" refers to a breeding method by which a (single) trait, such as clubroot resistance, can be transferred from one genetic background (a "donor") into another genetic background (i.e. the background of a "recurrent parent"), e.g. a plant not comprising such a CrS gene or locus. An offspring of a cross (e.g. an F1 plant obtained by crossing a CrS containing with a CrS lacking plant; or an F2 plant or F3 plant, etc., obtained from selfing the F1) is "backcrossed" to the parent ("recurrent parent"). After repeated backcrossing (BC1, BC2, etc.) and optionally selfings (BC1F1, BC2F1, etc.), the trait of the one genetic background is incorporated into the other genetic background.

"Marker assisted selection" or "MAS" is a process of using the presence of molecular markers, which are genetically linked to a particular locus or to a particular chromosome region (e.g. introgression fragment), to select plants for the presence of the specific locus or region (introgression fragment). For example, a molecular marker genetically and/or physically linked to a CrS locus, can be used to detect and/or select plants comprising the CrS locus. The closer the genetic linkage of the molecular marker to the locus, the less likely it is that the marker is dissociated from the locus through meiotic recombination.

"LOD-score" (logarithm (base 10) of odds) refers to a statistical test often used for linkage analysis in animal and plant populations. The LOD score compares the likelihood of obtaining the test data if the two loci (molecular markers loci and/or a phenotypic trait locus) are indeed linked, to the likelihood of observing the same data purely by chance. Positive LOD scores favor the presence of linkage and a LOD score greater than 3.0 is considered evidence for linkage. A LOD score of +3 indicates 1000 to 1 odds that the linkage being observed did not occur by chance.

A "molecular marker", or a "marker", as used herein, refers to a polymorphic locus, i.e. a polymorphic nucleotide (a so-called single nucleotide polymorphism or SNP; also called a polymorphic base) or a polymorphic DNA sequence (which can be insertion of deletion of a specific DNA sequence at a specific locus, or polymorphic DNA sequences). A marker refers to a measurable, genetic characteristic with a fixed position in the genome, which is normally inherited in a Mendelian fashion, and which can be used for mapping of a trait of interest. Thus, a molecular marker may be a short DNA sequence, such as a sequence surrounding a single base-pair change, i.e. a single nucleotide polymorphism or SNP, or a long DNA sequence, such as microsatellites or Simple Sequence Repeats (SSRs). The nature of the marker is dependent on the molecular analysis used and can be detected at the DNA, RNA or protein level. Genetic mapping can be performed using molecular markers such as, but not limited to, RFLP (restriction fragment length polymorphisms; Botstein et al. (1980), Am J Hum Genet 32:314-331; Tanksley et al. (1989), Bio/Technology 7:257-263), RAPD [random amplified polymorphic DNA; Williams et al. (1990), NAR 18:6531-6535], AFLP [Amplified Fragment Length Polymorphism; Vos et al. (1995) *NAR* 23:4407-4414], SSRs or microsatellites [Tautz et al. (1989), *NAR* 17:6463-6471]. Appropriate primers or probes are dictated by the mapping method used.

A marker can be identified by the identity of the 5' flanking sequence of the polymorphic locus, the polymorphic locus (which can be a polymorphic base in a SNP), and the 3' flanking region of the polymorphic locus.

As used herein, the markers indicated as "marker M1", "Marker M2" to "Marker Mx", or "M1", "M2" to "Mx" refer to the polymorphic locus (or the polymorphic base) as described herein above.

The term "marker allele" refers to the version of the marker (i.e. the version of the polymorphic locus) that is present in a particular plant at one of the chromosomes. Typically, a marker can exist as or can be said to have or to comprise two marker alleles. The term "haplotype", as used herein, refers to a specific combination of marker alleles as present within a certain plant or group of (related) plants. As described herein, a marker allele can be the version of the marker that is present in the resistant line (CrS clubroot resistance marker allele). The version of the same marker that is present in the susceptible line can be referred to as CrS clubroot susceptibility marker allele.

As used herein, the markers are indicated as "marker M1/R", "Marker M2/R" to "Marker Mx/R", or "M1/R", "M2/R" to "Mx/R" refer to the marker allele (or, the version of the polymorphic locus) that is present in the Resistant source (or Resistant donor line). Examples of marker alleles for the resistant source, containing the polymorphic base of the resistance source, are given in Table 9.

As used herein, the markers are indicated as "marker M1/S", "Marker M2/S" to "Marker Mx/S", or "M 1/R", "M2/S" to "Mx/S" refer to the marker allele that is present in the Susceptible line (or Susceptible parent).

Examples of marker alleles for the susceptible source, containing the polymorphic base of the susceptible line, are given in Table 9.

It will be clear that when reference herein is made to a certain SNP genotype or SNP allele (or marker genotype or marker allele) in a specific genomic sequence according to the invention, this encompasses also the SNP genotype or allele in variants of the genomic sequence, i.e. the SNP genotype or allele in a genomic sequence that is homologous, e.g. comprising at least 85%, 90%, 95%, 98%, 99% (substantial) sequence identity or more to the sequence referred to, such as the sequence of the markers according to the invention. Thus any reference herein to any one of SEQ ID NO: 1 to 22 in one aspect also encompasses a variant (homologous sequence) of any one of SEQ ID NO: 1 to 22, said variant comprising at least 85%, 90%, 95%, 98%, 99% sequence identity or more to said sequence (using e.g. the program 'Needle'), but comprising said SNP (marker) genotype or allele.

The term "AFLP®" (AFLP® is a registered trademark of KeyGene N.V., Wageningen, The Netherlands), "AFLP analysis" and "AFLP marker" is used according to standard terminology [Vos et al. (1995), NAR 23:4407-4414; EP0534858; world wide web at keygene.com/keygene/techs-apps/]. Briefly, AFLP analysis is a DNA fingerprinting technique which detects multiple DNA restriction fragments by means of PCR amplification. The AFLP technology usually comprises the following steps: (i) the restriction of the DNA with two restriction enzymes, preferably a hexa-cutter and a tetra-cutter, such as EcoRI, Pstl and Msel; (ii) the ligation of double-stranded adapters to the ends of the restriction fragments, such as EcoRI, PstI and Msel adaptors; (iii) the amplification of a subset of the restriction fragments using two primers complementary to the adapter and restriction site sequences, and extended at their 3' ends by one to three "selective" nucleotides, i.e., the selective amplification is achieved by the use of primers that extend into the restriction fragments, amplifying only those fragments in which the primer extensions match the nucleotides flanking the restriction sites. AFLP primers thus have a specific sequence and each AFLP primer has a specific code (the primer codes and their sequences can be found at the Keygene website: world wide web at keygene.com/keygene/pdf/PRIMERCO.pdf; herein incorporated by reference); (iv) gel electrophoresis of the amplified restriction fragments on denaturing slab gels or cappilaries; (v) the visualization of the DNA fingerprints by means of autoradiography, phosphor-imaging, or other methods. Using this method, sets of restriction fragments may be visualized by PCR without knowledge of nucleotide sequence. An AFLP marker, as used herein, is a DNA fragment of a specific size, which is generated and visualized as a band on a gel by carrying out an AFLP analysis. Each AFLP marker is designated by the primer combination used to amplify it, followed by the approximate size (in base pairs) of the amplified DNA fragment. It is understood that the size of these fragments may vary slightly depending on laboratory conditions and equipment used. Every time reference is made herein to an AFLP marker by referring to a primer combination and the specific size of a fragment, it is to be understood that such size is approximate, and comprises or is intended to include the slight variations observed in different labs. Each AFLP marker represents a certain locus in the genome.

The term "SSR" refers to Simple Sequence Repeats or microsatellite [Tautz et al. (1989), *NAR* 17:6463-6471]. Short Simple Sequence stretches occur as highly repetitive elements in all eukaryotic genomes. Simple sequence loci usually show extensive length polymorphisms. These simple sequence length polymorphisms (SSLP) can be detected by polymerase chain reaction (PCR) analysis and be used for identity testing, population studies, linkage analysis and genome mapping.

It is understood that molecular markers can be converted into other types of molecular markers. When referring to a specific molecular marker in the present invention, it is understood that the definition encompasses other types of molecular markers used to detect the genetic variation originally identified by the specific molecular markers. For example, if an AFLP marker is converted into another molecular marker using known methods, this other marker is included in the definition. For example, AFLP markers can be converted into sequence-specific markers such as, but not limited to STS (sequenced-tagged-site) or SCAR (sequence-characterized-amplified-region) markers using standard technology as described in Meksem et al. [2001), *Mol Gen Genomics* 265(2):207-214], Negi et al. [(2000), *TAG* 101: 146-152], Barret et al. (1989), *TAG* 97:828-833], Xu et al. [2001), *Genome* 44(1):63-70], Dussel et al. [(2002), *TAG* 105:1190-1195] or Guo et al. [(2003), *TAG* 103:1011-1017]. For example, Dussel et al. [(2002), *TAG* 105:1190-1195] converted AFLP markers linked to resistance into PCR-based sequence tagged site markers such as indel (insertion/deletion) markers and CAPS (cleaved amplified polymorphic sequence) markers.

Suitable molecular markers are, for example SNP markers (Single Nucleotide Polymorphisms), AFLP markers, microsatellites, minisatellites, Random Amplified Polymorphic DNA's (RAPD) markers, RFLP markers, Sequence Characterized Amplified Regions (SCAR) markers, and others, such as TRAP markers described by Hu et al. 2007, Genet Resour Crop Evol 54: 1667-1674).

Methods and assays for marker detection, or for analyzing the genomic DNA for the presence of a marker, are widely known in the art. The presence of a marker can, for example be detected in hybridization-based methods (e.g. allele-specific hybridization), using Taqman, Invader, PCR-based methods, oligonucleotide ligation-based methods, or sequencing-based methods.

A useful assay for detection of SNP markers is for example Kompetitive Allele-Specific PCR. For developing the KASP-assay 70 or more base pairs upstream and 70 or more basepairs downstream of the SNP are selected and two allele-specific forward primers and one allele specific reverse primer is designed. See e.g. Allen et al. 2011, Plant Biotechnology J. 9, 1086-1099, especially p1097-1098 for KASP assay method (incorporated herein by reference).

Other methods for detecting SNPs and Indels include methods based on extension of a single base of a probe-nucleic acid hybrid. These SNP detection methods are based on hybridization of a probe, which is adjacent to the polymorphism and which is identical for both alleles, and extension of a nucleotide to incorporate a detectable nucleotide residue upon extension of the primer. A detectable signal from the added nucleotide is used to determine the identity of the added nucleotide, from which the identity of the relevant allele is determined. See, e.g. Gunderson et all., 2006, Methods Enzymol 410:359 (incorporated herein by reference).

A "molecular marker linked to the CrS clubroot resistance locus", or a "molecular marker linked to the presence of the CrS clubroot resistance locus" as used herein refers to a molecular marker in a region in the genome that inherits with the CrS clubroot resistance locus as a single genetic unit in at least 50% of the cases. Thus, in this respect, the term linked can be a separation of about 50 cM, or less such as about 40 cM, about 30 cM, about 20 cM, about 10 cM, about 7.5 cM, about 6 cM, about 5 cM, about 4 cM, about 3 cM, about 2.5 cM, about 2 cM, or even less. Particular examples of markers linked to the CrS clubroot resistance locus are specified in Table 8. Said "molecular marker linked to the CrS clubroot resistance locus" is thus a marker which is linked to the CrS clubroot resistance gene.

A "molecular marker linked to the CrS clubroot resistance locus", or a "molecular marker linked to the presence of the CrS clubroot resistance locus" can also be a marker within 10 cM, within 7.5 cM, within 6 cM, within 5 cM, within 4 cM, within 3 cM, within 2.5 cM, within 2 cM, or within 1 cM, or within 0.5 cM, of the marker interval between and including markers M4 to M 5, or between and including markers M4 to M5, or between and including markers M4 to M7, or between and including markers M4 to M11. Such molecular markers can be markers located in a marker interval between and including markers M4 to M5, or between and including markers M4 to M7, or between and including markers M4 to M11. Such a marker can thus be any marker at a position on a chromosome within 10 cM of the marker interval from M4 to M11, including markers M4 and M11. Examples of markers located in a marker interval between and including markers M4 and M11 are the markers as specified in Table 8.

"Brassicaceae" or "Brassicaceae plant" as used herein refers to plants belonging to the family of Brassicaceae plants, also called Cruciferae family. Examples of Brassicaceae are, but are not limited to, *Brassica* species, such as *Brassica napus, Brassica oleracea, Brassica rapa, Brassica carinata, Brassica nigra*, and *Brassica juncea*; *Raphanus* species, such as *Raphanus caudatus, Raphanus raphanistrum*, and *Raphanus sativus*; *Matthiola* species; *Cheiranthus* species; *Camelina* species, such as *Camelina sativa*; *Crambe* species, such as *Crambe abyssinica* and *Crambe hispanica*; *Eruca* species, such as *Eruca vesicaria*; *Sinapis* species such as *Sinapis alba*; *Diplotaxis* species; *Lepidium* species; *Nasturtium* species; *Orychophragmus* species; *Armoracia* species, *Eutrema* species; *Lepidium* species; and *Arabidopsis* species.

A "*Brassica* plant" refers to allotetraploid or amphidiploid *Brassica napus* (AACC, 2n=38), *Brassica juncea* (AABB, 2n=36), *Brassica carinata* (BBCC, 2n=34), or to diploid *Brassica rapa* (syn. *B. campestris*) (AA, 2n=20), *Brassica oleracea* (CC, 2n=18) or *Brassica nigra* (BB, 2n=16).

"Oilseed rape" or "*Brassica* oilseed" or "oilseed crop" refers to oilseed rape cultivated as a crop, such as *Brassica napus, Brassica rapa, Brassica juncea*, or *Brassica carinata*.

"Winter oilseed rape" or "WOSR" is *Brassica* oilseed which is planted in late summer to early autumn, overwinters, and is harvested the following summer. WOSR generally requires vernalization to flower.

"Spring oilseed rape" or "SOSR" is *Brassica* oilseed which is planted in the early spring and harvested in late summer. SOSR does not require vernalization to flower.

"Erucic acid" as used herein is a monounsaturated omega-9 fatty acid, denoted 22:1ω9, or 22:1.

"Low erucic" or "low erucic acid" is less than 2% erucic acid in the seed oil.

"Canola quality" or "canola quality oil" is an oil that contains less than 2% erucic acid, and less than 30 micromoles of glucosinolates per gram of air-dried oil-free meal.

A "biological sample" can be a plant or part of a plant such as a plant tissue or a plant cell.

"Providing genomic DNA" as used herein refers to providing a sample comprising genomic DNA from the plant. The sample can refer to a tissue sample which has been obtained from said plant, such as, for example, a leaf sample, comprising genomic DNA from said plant. The sample can further refer to genomic DNA which is obtained from a tissue sample, such as genomic DNA which has been obtained from a tissue, such as a leaf sample. Providing genomic DNA can include, but does not need to include, purification of genomic DNA from the tissue sample. Providing genomic DNA thus also includes obtaining tissue material from a plant or larger piece of tissue and preparing a crude extract or lysate therefrom.

A "kit", as used herein, refers to a set of reagents for the purpose of performing the method of the invention, more particularly, the identification of the CrS clubroot resistance genes in biological samples or the determination of the zygosity status of plant material comprising the CrS clubroot resistance genes. More particularly, a preferred embodiment of the kit of the invention comprises at least two specific primers for identification of the CrS clubroot resistance genes, or at least two or three specific primers for the determination of the zygosity status. Optionally, the kit can further comprise any other reagent. Alternatively, according to another embodiment of this invention, the kit can comprise at least one specific probe, which specifically hybridizes with nucleic acid of biological samples to identify the presence of the CrS clubroot resistance genes therein, or at least two or three specific probes for the determination of the zygosity status. Optionally, the kit can further comprise any other reagent (such as but not limited to hybridizing buffer, label) for identification of the CrS clubroot resistance genes in biological samples, using the specific probe.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a specific nucleic acid sequence under the conditions set forth in the method (such as the conditions of the PCR identification protocol), whereby the specificity is determined by the presence of positive and negative controls.

"Isolated DNA" as used herein refers to DNA not occurring in its natural genomic context, irrespective of its length and sequence. Isolated DNA can, for example, refer to DNA which is physically separated from the genomic context, such as a fragment of genomic DNA. Isolated DNA can also be an artificially produced DNA, such as a chemically synthesized DNA, or such as DNA produced via amplification reactions, such as polymerase chain reaction (PCR) well-known in the art. Isolated DNA can further refer to DNA present in a context of DNA in which it does not occur naturally. For example, isolated DNA can refer to a piece of DNA present in a plasmid. Further, the isolated DNA can refer to a piece of DNA present in another chromosomal context than the context in which it occurs naturally, such as for example at another position in the genome than the natural position, in the genome of another species than the species in which it occurs naturally, or in an artificial chromosome.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents (especially the fruit dehiscence properties), such as seed obtained by selfing or crossing, e.g. hybrid seed (obtained by crossing two inbred parental lines), hybrid plants and plant parts derived there from are encompassed herein, unless otherwise indicated.

"Creating propagating material", as used herein, relates to any means know in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling), sexual reproduction (crossing with another plant) and asexual reproduction (e.g. apomixis, somatic hybridization).

For the purpose of this invention, the "sequence identity" of two related nucleotide or amino acid sequences, expressed as a percentage, refers to the number of positions in the two optimally aligned sequences which have identical residues (x100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6):276-277; see e.g. world wide web at ebi.ac.uk/emboss/align/index.html) using default settings (gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62. It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

As used herein "comprising" is to be interpreted as specifying the presence of the stated features, integers, steps or components as referred to, but does not preclude the presence or addition of one or more features, integers, steps or components, or groups thereof Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a nucleic acid which is functionally or structurally defined, may comprise additional DNA regions etc.

DETAILED DESCRIPTION

The current invention is based on the identification of a CrS clubroot resistance locus in Brassica. Surprisingly, it was found that the CrS clubroot resistance locus could be introgressed in elite Brassica varieties, and that lines with low erucic acid could be obtained.

In a first embodiment of the invention, a *Brassica* plant is provided comprising <2% erucic acid in the seed oil, and comprising a CrS clubroot resistance locus in a chromosomal segment comprising the marker M4. In another embodiment, said CrS clubroot resistance locus is in a chromosomal segment comprising the marker interval from marker M4 to M5. In another embodiment, said CrS clubroot resistance locus is in a chromosomal segment comprising the marker interval from marker M4 to M8, whereas in a further embodiment said CrS clubroot resistance locus is in a chromosomal segment comprising the marker interval from marker M4 to M11. In yet another embodiment, the plant according to the invention comprises the marker allele M4/R, whereas in yet another embodiment the plant according to the invention comprises the marker alleles M4/R and M5/R, or comprises the marker alleles M4/R, M5/R, M6/R and M7/R.

The plant according to the invention may contain <2% erucic acid, or <1.5% erucic acid, or <1% erucic acid, or 0% erucic acid.

The marker interval can be the region as present in the CrS donor on the genetic map from 55.49 to 57.50 cM, or from 55.49 to 55.67 cM, or from 55.49 to 58.77 cM, or from 55.49 to 59.14 cM, or from 55.49 to 59.32 cM, or from 55.49 to 66.98 cM on the genetic map as shown herein in the Examples. It is understood that marker M4 can be the marker allele M4/R or wherein the marker allele for marker M4 is "A", that marker M5 can be the marker allele M5/R or wherein the marker allele for marker M5 is "T" that marker M6 can be the marker allele M6/R or wherein the marker allele for marker M6 is G, that marker M7 can be the marker allele M7/R or wherein the marker allele for marker M7 is T. Further, it is understood that marker M8 can be the marker allele M8/R or wherein the marker allele for marker M8 may be C, marker M9 can be the marker allele M9/R or wherein the marker allele for marker M9 may be T, marker M10 can be the marker allele M10/R or wherein the marker allele for marker M10 may be A, marker M11 can be the marker allele M11/R or wherein the marker allele for marker M11 may be "A".

The marker interval can be the region as present in the CrS donor that corresponds to the region from position 10,369,430 bp to position 10,375,744, or from position 10,369,430 to position 9,699,466 bp, or from position 10,369,430 bp to position 933,572 bp on the Darmor-bzh (version 8.1) genome sequence as described by Bayer et al., 2017, Plant Biotech J. 15, p. 1602, wherein the base at position 10,369,430 bp is an A; the base at position 10,3757, 44 bp is a T, and, optionally, the base at position 9,801,311 is G and, optionally, the base at position 9,699,466 bp is a T, and, optionally, the base at position 933,572 bp is an A.

The *Brassica* plant according to the invention may comprise any additional marker in the marker interval, such as M5 and/or M6.

The CrS clubroot resistance locus can be comprised in the marker interval from marker M4 to M5, or in the marker interval from M4 to M6, or in the marker interval from M4 to M7, or in the marker interval from marker M4 to M8, or in the marker interval from marker M4 to M9, or in the marker interval from marker M4 to M10, or in the marker interval from marker M4 to M11.

The CrS clubroot resistance gene, or CrS resistance gene, or CrS gene is located in the CrS clubroot resistance locus. In other words, the CrS clubroot resistance locus refers to the genetic locus that comprises a CrS clubroot resistance gene.

*Brassica* seeds comprising the CrS clubroot resistance locus have been deposited at the NCIMB (NCIMB Ltd, Ferguson Building, Craibstone Estate, Bucksburn, Aberdeen AB21 9YA, Scotland, UK) on Jan. 21, 2019, under accession number NCIMB 43341.

A chromosomal interval flanked by the markers as described herein, are for example the markers as listed in Tables 3 and 8 below between the specifically mentioned markers, or other markers that are not explicitly shown, but which are also flanked by the marker pairs mentioned. The skilled person can easily identify new markers in the genomic region region being flanked by any of the marker pairs listed above. Such markers need not to be SNP markers, but can be any type of genotypic or phenotypic marker mapped to that genomic or subgenomic region. Preferably such markers are genetically and physically linked to the presently described CrS locus according to the invention. The markers are preferably indicative of the presence of the CrS locus in a non-source specific manner.

In another embodiment, the *Brassica* plant according to the invention does not comprise the marker allele M3/R, or M2/R, or M1/R, or a combination thereof.

It is understood that plants in which the chromosomal interval at the left side of marker M4 is derived from the susceptible recurrent parent do not contain the high erucic phenotype from the resistant donor parent.

The *Brassica* plant according to the invention may also be a plant not comprising the marker allele M3/R, not comprising the marker allele M2/R, not comprising marker allele M1/R, not comprising marker allele M3/R and M1/R, or not comprising marker allele M2/R and marker allele M1/R. The *Brassica* plant according to the invention may not comprise the chromosomal segment derived from a CrS donor parent at the left side of marker M3, or at the left side of marker M2. The *Brassica* plant according to the invention may not comprise the chromosomal segment derived from a CrS donor parent downstream of and including the position corresponding to position 11,256,444 bp of the Darmor-bzh (version 8.1) genome sequence as described by Bayer et al., supra. The *Brassica* plant according to the invention may not comprise the chromosomal segment derived from a CrS donor parent at the left side of the genetic position corresponding to the genetic position of 53.14 cM with reference to the genetic map as described herein in the Examples. The plant may thus not comprise the marker allele "A" of marker M3, and/or may not comprise the marker allele "A" of marker M2, and/or may not comprise the marker allele "T" of marker M1.

"M1/R" as defined herein is the marker allele of marker M1 in which the polymorphic base is "T".

"M1/S" as defined herein is the marker allele of marker M1 in which the polymorphic base is "C".

"M2/R" as defined herein is the marker allele of marker M2 in which the polymorphic base is "A".

"M2/S" as defined herein is the marker allele of marker M2 in which the polymorphic base is "G".

"M3/R" as defined herein is the marker allele of marker M3 in which the polymorphic base is "A".

"M3/S" as defined herein is the marker allele of marker M3 in which the polymorphic base is "G".

"M4/R" as defined herein is the marker allele of marker M4 in which the polymorphic base is "A".

"M4/S" as defined herein is the marker allele of marker M4 in which the polymorphic base is "C".

"M5/R" as defined herein is the marker allele of marker M5 in which the polymorphic base is "T".

"M5/S" as defined herein is the marker allele of marker M5 in which the polymorphic base is "C".

"M6/R" as defined herein is the marker allele of marker M6 in which the polymorphic base is "G".

"M6/S" as defined herein is the marker allele of marker M6 in which the polymorphic base is "A".

"M7/R" as defined herein is the marker allele of marker M7 in which the polymorphic base is "T".

"M7/S" as defined herein is the marker allele of marker M7 in which the polymorphic base is "C".

"M8/R" as defined herein is the marker allele of marker M8 in which the polymorphic base is "C".

"M8/S" as defined herein is the marker allele of marker M8 in which the polymorphic base is "T".

"M9/R" as defined herein is the marker allele of marker M9 in which the polymorphic base is "T".

"M9/S" as defined herein is the marker allele of marker M9 in which the polymorphic base is "C".

"M10/R" as defined herein is the marker allele of marker M10 in which the polymorphic base is "A".

"M10/S" as defined herein is the marker allele of marker M10 in which the polymorphic base is "G".

"M11/R" as defined herein is the marker allele of marker M11 in which the polymorphic base is "A".

"M11/S" as defined herein is the marker allele of marker M11 in which the polymorphic base is "G".

In yet another embodiment, the *Brassica* plant according to the invention is a *Brassica napus* or a Brassica rapa plant, whereas in yet another embodiment, the *Brassica* plant according to the invention is a Brassica napus WOSR plant or a *Brassica napus* SOSR plant.

In another aspect the *Brassica* plant according to the invention is a *Brassica napus* WOSR plant wherein said chromosomal segment comprises the marker interval from marker M4 to M7. In yet another aspect the *Brassica* plant according to the invention is a *Brassica napus* SOSR plant wherein said chromosomal segment comprises the marker interval from marker M4 to M5, such as a *Brassica napus* SOSR plant comprising the marker interval from marker M4 to M8, such as a *Brassica napus* SOSR plant wherein said chromosomal segment is obtainable from reference seeds deposited at NCIMB under accession number NCIMB 43341.

The *Brassica napus* WOSR plant may comprise a CrS clubroot resistance locus in a chromosomal segment comprising the marker interval from marker M4 to M9, or from marker M4 to M10, or from marker M4 to M11. The *Brassica napus* WOSR plant may not comprise the marker allele M2/R, or may not comprise marker alleles M2/R and M1/R. Said *Brassica napus* WOSR plant may not comprise the chromosomal segment derived from a CrS donor parent at the left side of marker M3, or at the left side of marker M2, or downstream of the position corresponding to position 11,256,444 bp of the Darmor-bzh (version 8.1) genome sequence as described by Bayer et al., supra, or downstream of position 12,499,060 bp of the Darmor-bzh (version 8.1) genome sequence as described by Bayer et al., supra, or at the left side of the genetic position corresponding to the genetic position of 53.14 cM with reference to the genetic map as described herein in the Examples, or at the left side of the genetic position corresponding to position 51.99 cM with reference to the genetic map as described herein in the Examples.

The *Brassica napus* SOSR plant may comprise a CrS clubroot resistance locus in a chromosomal segment comprising the marker interval from marker M4 to M5, or from marker M4 to M6, or from marker M4 to M7, or from marker M4 to M8, or from marker M4 to M9, or from marker M4 to M10, or from marker M4 to M11. The *Brassica napus* SOSR plant may not comprise marker allele M3/R, or may not comprise marker alleles M3/R and M1/R. Said *Brassica napus* SOSR plant may not comprise the chromosomal segment derived from a CrS donor parent at the left side of marker M3, or downstream of the position corresponding to position 11,256,444 of the Darmor-bzh (version 8.1) genome sequence as described by Bayer et al., supra, or at the left side of the genetic position corresponding to the genetic position of 53.14 cM with reference to the genetic map as described herein in the Examples.

It will be clear that the plants according to the invention, comprising a CrS clubroot resistance locus, may contain the marker alleles from the resistant source (from the CrS donor parent) in the specified marker interval. For example, plants comprising a CrS clubroot resistance locus in a chromosomal segment comprising the marker interval from marker M4 to M7 may contain the marker alleles M4/R and M7/R, or may contain the marker alleles M4/R, M5/R, M6/R and M7/R. Said plants may further comprise marker allele M8/R, and, optionally, marker allele M9/R, and, optionally, marker allele M10/R, and, optionally, marker allele M11/R.

In another aspect, the *Brassica* plant according to the invention is resistant to P. brassicae pathotypes P2, P3, P5, P6 or P8 or to isolate CR11. The *Brassica* plant may also be resistant to some of the recently identified pathotypes including 2B, 3A, 5X, and 8P based on the Canadian Clubroot Differential set (CCD)

Strelkov et al. 2018, Can J Plant Pathology pp 284.

In yet another aspect, the *Brassica* plant according to the invention is heterozygous for said clubroot resistance locus, whereas in another aspect, the *Brassica* plant according to the invention is homozygous for said clubroot resistance locus.

Yet another embodiment provides the *Brassica* plant according to the invention which further comprises a gene conferring herbicide tolerance. In another embodiment, the gene conferring herbicide tolerance tolerance is a gene which confers resistance to glufosinate or to glufosinate ammonium or a gene conferring resistance to glyphosate.

The gene conferring herbicide resistance may be the bar or pat gene, which confer resistance to glufosinate ammonium (Liberty®, Basta® or Ignite®) [EP 0 242 236 and EP 0 242 246 incorporated by reference]; or any modified EPSPS gene, such as the 2mEPSPS gene from maize [EP 0 508 909 and EP 0 507 698 incorporated by reference], or glyphosate acetyltransferase, or glyphosate oxidoreductase, which confer resistance to glyphosate (RoundupReady®), or bromoxynitril nitrilase to confer bromoxynitril tolerance, or any modified AHAS gene, which confers tolerance to sulfonylureas, imidazolinones, sulfonylaminocarbonyltriazolinones, triazolopyrimidines or pyrimidyl(oxy/thio)benzoates, such as oilseed rape imidazolinone-tolerant mutants PM1 and PM2, currently marketed as Clearfield® canola. Further, the plants according to the invention may additionally contain an endogenous or a transgene which confers increased oil content or improved oil composition, such as a 12:0 ACP thioesteraseincrease to obtain high laureate, which confers pollination control, such as such as barnase under control of an anther-specific promoter to obtain male sterility, or barstar under control of an anther-specific promoter to confer restoration of male sterility, or such as the Ogura cytoplasmic male sterility and nuclear restorer of fertility.

The plants according to the invention which additionally contain a gene which confers resistance to glufosinate ammonium (Liberty®, Basta® or Ignite®) may contain a gene coding for a phosphinothricin-N-acetyltransferase (PAT) enzyme, such as a coding sequence of the bialaphos resistance gene (bar) of Streptomyces hygroscopicus. Such plants may, for example, comprise the elite events MS-BN1 and/or RF-BN1 as described in WO01/41558, or elite event MS-B2 and/or RF-BN1 as described in WO01/31042 or in WO2014/170387, or any combination of these events.

The plants according to the invention which contain a gene which confers resistance to glyphosate (RoundupReady®) may contain a glyphosate resistant EPSPS, such as a CP4 EPSPS, or an N-acetyltransferase (gat) gene. Such plants may, for example, comprise the elite event RT73 as described in WO02/36831, or elite event MON88302 as described in WO11/153186, or event DP-073496-4 as described in WO2012/071040.

The plants according to the invention may further be canola quality plants.

Seeds of the plants according to the invention are also provided.

Another aspect of the invention provides a method for producing a clubroot resistant *Brassica* plant, said method comprising (a) identifying at least one *Brassica* plant comprising a CrS clubroot resistance locus with at least one marker within 10 cM of the marker interval from M4 to M5, and (b) selecting a plant comprising said CrS clubroot resistance locus. In a further embodiment, said method comprising identifying at least one *Brassica* plant comprising at least one marker in the marker interval from M4 to M11, and not comprising the marker allele M3/R or not comprising marker allele M2/R, or not comprising marker allele M1/R, whereas in another embodiment, said *Brassica* plant is identified using markers in the marker interval from M4 to M5.

Another embodiment of the invention provides a method for producing a clubroot resistant *Brassica* plant, said method comprising (a) crossing a first *Brassica* plant comprising a CrS clubroot resistance locus with a second plant; and (b) identifying a progeny plant comprising at least one marker within 10 cM of the marker interval from M4 to M5. In a further embodiment, said method comprises identifying a progeny plant comprising at least one marker in the marker interval from M4 to M11, and not comprising the marker allele M3/R or not comprising marker allele M2/R, or not comprising marker allele M1/R.

Presence of the CrS clubroot resistance locus can be identified using molecular markers.

A marker within 10 cM of the marker interval from M4 to M5 can be a marker within 10 cM, or 8 cM, or 5 cM, or 3 cM, or 2 cM, or 1 cM, or 0.5 cM of the interval from M4 to M5, or can be a marker within the interval from M4 to M11, or can be a marker within the interval from M4 to M10, or can be a marker within the interval from M4 to M9, or can be a marker within the interval from M4 to M8, or can be a marker within the interval from M4 to M7, or can be a marker within the interval from M4 to M6, or can be a marker within the interval from M4 to M5. A marker within 10 cM of the marker interval from M4 to M5 can comprise any one of markers M4, M5, M6, M7, M8, M9, M10 and M11.

Suitable are markers that are linked to the CrS clubroot resistance locus can be developed using methods known in the art. New markers suitable for the invention can be developed based on the genetic information of the CrS locus. It is understood that such markers can be developed by comparing the sequence of the CrS clubroot resistance locus from the resistant *Brassica* line with the sequence of the same locus in a susceptible *Brassica* line; identifying a specific sequence region in the CrS clubroot resistance locus which does not occur in the corresponding locus of the susceptible Brassica line. A molecular marker linked to the CrS clubroot resistance locus can thus be a marker detecting the presence of the CrS clubroot resistance locus. A molecular marker linked to the CrS clubroot resistance locus can also be a marker in the sequences flanking the CrS clubroot resistance locus, which is polymorphic between lines comprising the CrS clubroot resistance locus and lines lacking, but which inherits with the CrS clubroot resistance locus as a single genetic unit in at least 50% of the cases. Suitable markers to detect the presence of the CrS clubroot resistance locus any one of the markers M4, M5, M6, M7, M8, M9, M10, and M11.

Markers suitable to determine the presence of the CrS clubroot resistance locus can be the markers that are linked to CrS clubroot resistance locus, such as the markers the of Table 8, in particular the CrS clubroot resistance marker alleles which are polymorphic between the resistant donor parent and the susceptible recurrent parent.

It is understood that plants comprising the CrS clubroot resistance locus can be performed by the identification of the presence of the marker alleles M4/R, M5/R, M6/R, M7/R, M8/R, M9/R, M10/R, and M11/R.

The absence of the CrS clubroot resistance locus can be determined by the absence of marker alleles that are linked to the presence of the CrS clubroot resistance locus (CrS clubroot resistance marker alleles), such as by the absence of the CrS clubroot resistance marker alleles of Table 8 with the polymorphic base detected in the resistant lines. Furthermore, markers suitable to determine the absence of the CrS clubroot resistance locus can be marker alleles which are linked to the CrS clubroot susceptibility locus (CrS clubroot susceptibility marker alleles; i.e. the alleles in the susceptible recurrent parent). Examples of CrS clubroot susceptibility marker alleles that are linked to the CrS clubroot susceptibility locus are the marker alleles of Table 8 with the polymorphic base detected in the Recurrent parent.

Absence of marker alleles can be determined by determining the absence of the specified marker alleles from the resistant source. Absence of marker alleles from the resistant source can, but must not, be determined by determining the presence of the corresponding marker allele from the susceptible line. For example, absence of the marker alleles M3/R, or M2/R, or M1/R can be determined by determining the presence of M3/S, or M2/S, or M1/S.

Analysis for the presence of markers according to the invention can be performed with a first primer and a second primer, and, optionally, a probe, selected from the group consisting of a first primer consisting of a sequence of 15 to 30 nucleotides, or 15 to 25 nucleotides, or 18 to 22 nucleotides of the CrS clubroot resistance genes according to the invention, a second primer being complementary to a sequence of 15 to 30 nucleotides, or 15 to 25 nucleotides, or 18 to 22 nucleotides of the CrS clubroot resistance genes according to the invention, and wherein the distance between said first and said second primer on the CrS clubroot resistance gene is between 1 and 400 bases, or between 1 and 150 bases, and wherein the first primer is located, with respect to the CrS coding sequence, upstream of said second primer, and a probe which is identical to at least 15 nucleotides, or at least 18 nucleotides, but not more than 25 nucleotides, or not more than 22 nucleotides of the sequence of the CrS clubroot resistance gene between said first and said second primer, provided that either the sequence of the first primer, or the sequence of the second primer, or the sequence of said probe is not present in the corresponding locus in a susceptible Brassica plant. Said probe may be labelled, such as, for example, described in U.S. Pat. No. 5,538,848.

Analysis for the presence of markers according to the invention can be performed with a first and second primer as described above recognizing both the CrS sequence and the corresponding locus in the susceptible Brassica line, a first probe recognizing a sequence of the CrS clubroot resistance gene as described above, but not recognizing a sequence between said first and said second primer in the susceptible Brassica line, and a second probe recognizing a sequence between said first and said second primer in the susceptible Brassica line, but not of the CrS clubroot resistance gene, and wherein said the label of the first probe is different from that of the second probe.

Further suitable primers for analysis of the presence of markers according to the invention are markers a first primer as described above recognizing both the CrS sequence and the corresponding locus in the susceptible *Brassica* line, a second primer recognizing the CrS sequence but not the corresponding locus in the susceptible *Brassica* line, and a third primer recognizing the corresponding locus in the susceptible *Brassica* line but not the CrS sequence. Said second and third primer may be labelled as indicated above, and said second primer may contain a label which is different from said third primer.

Identification of PCR products specific for the CrS clubroot resistance genes and for the corresponding locus in the susceptible *Brassica* line can occur e.g. by size estimation after gel or capillary electrophoresis (e.g. for the CrS clubroot resistance locus and for the corresponding locus in the susceptible *Brassica* line comprising a number of inserted or deleted nucleotides which results in a size difference between the fragments amplified from the CrS clubroot resistance locus and for the corresponding locus in the susceptible *Brassica*, such that said fragments can be visibly separated on a gel); by evaluating the presence or absence of the two different fragments after gel or capillary electrophoresis, whereby the diagnostic PCR amplification of the CrS clubroot resistance locus can, optionally, be performed separately from the diagnostic PCR amplification of the corresponding locus in the susceptible line; by direct sequencing of the amplified fragments; or by fluorescence-based detection methods.

Analysis for the presence of markers according to the invention can be performed with a probe that hybridizes to the bases immediately upstream of the marker, followed by a primer extension in which DNA polymerase extends the hybridized primer by adding a base that is complementary to the marker. The incorporated base is labelled and detected of the label specific for the incorporated base determines the marker allele.

In any of the above described methods or uses, the markers and marker alleles can localize to the same chromosomal intervals and can be selected from the same groups as described above for the other embodiments and aspect.

Also provided are any of the markers comprising an allele linked to the functional CrS gene located on chromosome A08, as described herein.

Also provided herein is a chromosome fragment, which comprises the CrS resistance gene, as described throughout the specification. In one aspect the chromosome fragment is isolated from its natural environment. In another aspect it is in a plant cell, especially in a *Brassica* cell. Also an isolated part of the chromosome fragment comprising the CrS resistance gene located on chromosome A08 is provided herein. Such a chromosome fragment can for example be a contig or a scaffold.

Also described is a chromosome fragment comprising the CrS clubroot resistance locus in a chromosomal segment comprising the marker interval from marker M4 to M5, said chromosomal fragment further comprising the marker alleles M3/S, or M2/S, or M1/S, or a combination thereof.

In another embodiment, a method is provided for producing a clubroot resistant *Brassica* plant comprising introducing the CrS clubroot resistance locus into a plant not comprising the CrS clubroot resistance locus using genome editing.

The CrS clubroot resistance locus can be introduced by exchanging the chromosomal segment comprising the CrS clubroot resistance locus, such as the chromosomal segment comprising the marker interval from marker M4 to M5, for the corresponding genomic segment in a *Brassica* plant not comprising the CrS resistance locus. Alternatively, the method can comprise determining the sequence of the CrS resistance locus, such as the chromosomal segment comprising the marker interval from marker M4 to M5, determining the sequence of the corresponding chromosomal segment of a *Brassica* plant not comprising the CrS resistance locus, and replacing the sequence of said chromosomal segment of said *Brassica* plant not comprising the CrS resistance locus with the sequence of said chromosomal segment of said CrS resistance locus using gene editing. Replacing the sequence can take place by exchanging the chromosomal fragment, or by making the individual changes in the sequence.

Accordingly, using these technologies, plants lacking a CrS gene can be converted to CrS clubroot resistant plants by making the desired changes to the existing locus that corresponds to the CrS locus, or alternatively to introduce one or more complete sequences of the CrS gene, e.g. as described herein, at the corresponding specific genomic location.

Genome editing, also called gene editing, genome engineering, as used herein, refers to the targeted modification of genomic DNA in which the DNA may be inserted, deleted, modified or replaced in the genome. Genome editing may use sequence-specific enzymes (such as endonuclease, nickases, base conversion enzymes) and/or donor nucleic acids (e.g. dsDNA, oligo's) to introduce desired changes in the DNA. Sequence-specific nucleases that can be programmed to recognize specific DNA sequences include meganucleases (MGNs), zinc-finger nucleases (ZFNs), TAL-effector nucleases (TALENs) and RNA-guided or DNA-guided nucleases such as Cas9, Cpf1, CasX, CasY, C2c1, C2c3, certain Argonaut-based systems (see e.g. Osakabe and Osakabe, Plant Cell Physiol. 2015 Mar;56(3):389-400; Ma et al., Mol Plant. 2016 Jul 6;9(7):961-74; Bortesie et al., Plant Biotech J, 2016, 14; Murovec et al., Plant Biotechnol J. 15:917-926, 2017; Nakade et al., Bioengineered Vol 8, No.3:265-273, 2017; Burstein et al., Nature 542, 37-241;

Komor et al., Nature 533, 420-424, 2016; all incorporated herein by reference). Donor nucleic acids can be used as a template for repair of the DNA break induced by a sequence specific nuclease. Donor nucleic acids can also be used as such for genome editing without DNA break induction to introduce a desired change into the genomic DNA.

It is another object of the invention to provide the use of at least one marker within 10 cM of the marker interval from M4 to M5 to identify a plant comprising the CrS clubroot resistance locus. It is another object of the invention to provide the use of markers M4, M5, M6, M7, M8, M9, M10 and/or M11 to identify a plant comprising the CrS clubroot resistance locus.

The markers that can be used to identify a plant comprising the CrS clubroot resistance locus can be marker M4, M5, M6, M7, M8, M9, M10 or M11 or any combination thereof. In a preferred embodiment, the markers that can be used to identify a plant comprising the CrS clubroot resistance locus can be marker M4, M5, M6 and/or M7. In another preferred embodiment, the marker M4 can be used to identify a plant comprising the CrS clubroot resistance locus.

Further, the markers flanking the CrS clubroot resistance locus at the left side can be used to identify plants with the CrS clubroot resistance locus and low erucic acid. Markers that can be used to identify plants with the CrS clubroot resistance locus and low erucic acid can be M3 not comprising the donor allele; M2 not comprising the donor allele; or marker M1 not comprising the donor allele.

In yet another aspect, a method is provided for the protection of a group of cultivated plants according to the invention in a field wherein weeds are controlled by the application of a composition comprising one or more herbicidal active ingredients. In a further aspect, said plants comprise a gene which confers resistance to glufosinate or to glufosinate ammonium or a gene conferring resistance to glyphosate, and the herbicide is glufosinate or glufosinate ammonium or glyphosate.

Hybrid seeds of the plants according to the invention may be generated by crossing two inbred parental lines, wherein one of the inbred parental lines comprises the CrS clubroot resistance genes according to the invention. The inbred line may comprise the CrS clubroot resistance gene in homozygous form. The hybrid may contain the CrS clubroot resistance gene in heterozygous form. In order to produce pure hybrid seeds one of the parental lines is male sterile and is pollinated with pollen of the other line. By growing parental lines in rows and only harvesting the F1 seed of the male sterile parent, pure hybrid seeds are produced. To generate male sterile parental lines, the system as described in EP 0,344,029 or U.S. Pat. No. 6,509,516 may be used, wherein a gene encoding a phytotoxic protein (barnase) is expressed under the control of a tapetum specific promoter, such as TA29, ensuring selective destruction of tapetum cells. Transformation of plants with the chimeric gene pTA29:barnase results in plants in which pollen formation is completely prevented [Mariani et al. (1990), *Nature* 347: 737-741]. Cytochemical and histochemical analysis of anther development of *Brassica napus* plants comprising the chimeric pTA29-barnase gene is described by De Block and De Brouwer [(1993), *Planta* 189:218-225]. To restore fertility in the progeny of a male-sterile plant the male-sterile plant (MS parent) is crossed with a transgenic plant (RF parent) carrying a fertility-restorer gene, which when expressed is capable of inhibiting or preventing the activity of the male-sterility gene [U.S. Pat. Nos. 5,689,041; 5,792,929; De Block and De Brouwer, supra]. The use of co-regulating genes in the production of male-sterile plants to increase the frequency of transformants having good agronomical performance is described in WO96/26283. Typically, when the sterility DNA encodes a barnase, the co-regulating DNA will encode a barstar, preferably an optimized barstar gene is used as described in published PCT patent application WO 98/10081. It is understood that different promoters may be used to drive barnase expression in order to render the plant male sterile. Likewise, barstar may be operably linked to different promoters, such as 35S from Cauliflower mosaic virus.

Male sterile plants can also be generated using other techniques, such as cytoplasmic male sterility/restorer systems [e.g. the Ogura system, published US patent application 20020032916, U.S. Pat. No. 6,229,072, WO97/02737, U.S. Pat. No. 5,789,566 or the Polima system of U.S. Pat. No. 6,365,798, WO98/54340 or the Kosena system of WO95/09910, U.S. Pat. No. 5,644,066].

Either the male sterile (MS) parent or the fertility restorer (RF) parent, or both, may comprise the CrS clubroot resistance genes according to the invention. This can be accomplished by either introducing the CrS clubroot resistance genes into an elite *B. napus* line and then introducing the male sterility or the fertility restorer. Alternatively the CrS clubroot resistance genes can be introduced directly into a MS or RF parent line, by crossing a plant comprising the CrS clubroot resistance genes with the MS parent or RF-parent.

The F1 hybrid seeds generated from the cross between the MS and RF parent will then contain the CrS clubroot resistance genes.

Suitable to the invention is an isolated nucleic acid molecule comprising the CrS clubroot resistance locus, wherein said CrS clubroot resistance locus localizes within an interval from M4 to M5. The isolated nucleic acid molecule as described herein may further be characterized as not comprising marker allele M3/R or not comprising marker allele M2/R, or not comprising marker allele M1/R.

In particular, the methods and kits according to the invention are suitable to determine the presence of the CrS clubroot resistance locus. The presence of the CrS clubroot resistance locus can be determined using at least one molecular marker, wherein said one molecular marker is linked to the presence of the CrS clubroot resistance locus as defined herein.

Kits can be provided containing primers and/or probes specifically designed to detect the marker alleles according to the invention. The components of the kits can be specifically adjusted, for purposes of quality control (e.g., purity of seed lots), detection of the presence or absence of the CrS clubroot resistance genes in plant material or material comprising or derived from plant material, such as but not limited to food or feed products. The zygosity status of the CrS clubroot resistance genes can be determined by using alternative sets of primers and/or probes that specifically the CrS locus and the corresponding locus in a susceptible *Brassica* line.

Suitable to the invention is a method to produce clubroot free Brassica plants, comprising the steps of sowing seeds from the Brassica plants according to the invention comprising a CrS clubroot resistance gene, growing the plants in the field, optionally spraying the plants with fungicides, and harvesting.

The CrS clubroot resistance locus according to the invention can be used to develop molecular markers by developing primers specifically recognizing sequences in the CrS clubroot resistance locus.

Also provided is a method of producing food, feed, or an industrial product, comprising obtaining the plant according to the invention or a part thereof and preparing the food, feed or industrial product from the plant or part thereof. In a further object, said food or feed is oil, meal, grain, starch, flour or protein; or said industrial product is biofuel, fiber, industrial chemicals, a pharmaceutical or a nutraceutical.

In some embodiments, the plant cells of the invention, i.e. a plant cell comprising a CrS clubroot resistance gene as well as plant cells generated according to the methods of the invention, may be non-propagating cells.

The obtained plants according to the invention can be used in a conventional breeding scheme to produce more plants with the same characteristics or to introduce the characteristic of the presence of the CrS gene according to the invention in other varieties of the same or related plant species, or in hybrid plants. The obtained plants can further be used for creating propagating material. Plants according to the invention can further be used to produce gametes, seeds (including crushed seeds and seed cakes), seed oil, embryos, either zygotic or somatic, progeny or hybrids of plants obtained by methods of the invention. Seeds obtained from the plants according to the invention are also encompassed by the invention.

All patents, patent applications, and publications or public disclosures (including publications on internet) referred to or cited herein are incorporated by reference in their entirety.

The sequence listing contained in the file named "190202_ST25.txt", which is 5 kilobytes (size as measured in Microsoft Windows®), contains xx sequences SEQ ID NO: 1 through SEQ ID NO: 22 is filed herewith by electronic submission and is incorporated by reference herein.

In the description and examples, reference is made to the following sequences:

| | |
|---|---|
| SEQ ID No. 1: | 5' flanking sequence of Marker 1 |
| SEQ ID No. 2: | 3' flanking sequence of Marker 1 |
| SEQ ID No. 3: | 5' flanking sequence of Marker 2 |
| SEQ ID No. 4: | 3' flanking sequence of Marker 2 |
| SEQ ID No. 5: | 5' flanking sequence of Marker 3 |
| SEQ ID No. 6: | 3' flanking sequence of Marker 3 |
| SEQ ID No. 7: | 5' flanking sequence of Marker 4 |
| SEQ ID No. 8: | 3' flanking sequence of Marker 4 |
| SEQ ID No. 9: | 5' flanking sequence of Marker 5 |
| SEQ ID No. 10: | 3' flanking sequence of Marker 5 |
| SEQ ID No. 11: | 5' flanking sequence of Marker 6 |
| SEQ ID No. 12: | 3' flanking sequence of Marker 6 |
| SEQ ID No. 13: | 5' flanking sequence of Marker 7 |
| SEQ ID No. 14: | 3' flanking sequence of Marker 7 |
| SEQ ID No. 15: | 5' flanking sequence of Marker 8 |
| SEQ ID No. 16: | 3' flanking sequence of Marker 8 |
| SEQ ID No. 17: | 5' flanking sequence of Marker 9 |
| SEQ ID No. 18: | 3' flanking sequence of Marker 9 |
| SEQ ID No. 19: | 5' flanking sequence of Marker 10 |
| SEQ ID No. 20: | 3' flanking sequence of Marker 10 |
| SEQ ID No. 21: | 5' flanking sequence of Marker 11 |
| SEQ ID No. 22: | 3' flanking sequence of Marker 11 |

Unless stated otherwise in the Examples, all recombinant techniques are carried out according to standard protocols as described in "Sambrook J and Russell D W (eds.) (2001) Molecular Cloning: A Laboratory Manual, 3rd Edition, Cold Spring Harbor Laboratory Press, New York" and in "Ausubel F A, Brent R, Kingston R E, Moore D D, Seidman J G, Smith J A and Struhl K (eds.) (2006) Current Protocols in Molecular Biology. John Wiley & Sons, New York".

Standard materials and references are described in "Croy RDD (ed.) (1993) Plant Molecular Biology LabFax, BIOS Scientific Publishers Ltd., Oxford and Blackwell Scientific Publications, Oxford" and in "Brown TA, (1998) Molecular Biology LabFax, 2nd Edition, Academic Press, San Diego". Standard materials and methods for polymerase chain reactions (PCR) can be found in "McPherson MJ and Mller SG (2000) PCR (The Basics), BIOS Scientific Publishers Ltd., Oxford" and in "PCR Applications Manual, 3rd Edition (2006), Roche Diagnostics GmbH, Mannheim or world wide web at.roche-applied-science.com".

It should be understood that a number of parameters in any lab protocol such as the PCR protocols in the below Examples may need to be adjusted to specific laboratory conditions, and may be modified slightly to obtain similar results. For instance, use of a different method for preparation of DNA or the selection of other primers in a PCR method may dictate other optimal conditions for the PCR protocol. These adjustments will however be apparent to a person skilled in the art, and are furthermore detailed in current PCR application manuals.

EXAMPLES

1. Clubroot Resistant Donor Development

From a segregating synthetic Brassica napus material, a screening for clubroot resistance was performed in growth chamber using clubroot field mix as inoculum. This allowed to select resistant plants and to characterize and name a single dominant resistant gene present as CrS from which a fixed line by DH approach was developed.

Inoculating Seedlings with a Spore Suspension

Plants were seeded in 36 cell disposable plastic trays with one plant per cell and placed in a plastic container with no holes underneath to prevent leaking and reduce risk of contaminating flows. An empty cell in each tray was left open for placing water into the tray so that plants take water from the roots. Plants were inoculated with a spore suspension by carefully dripping the spore suspension against the seedling stem at the seedling base 5-7 days after seeding. Plants were grown in a growth chamber at 20/16 C (day/night) temperature and 16 h photoperiod.

Disease Rating

For assessing clubroot severity plants were carefully removed from the soil and rated for disease severity on a 0 to 3 scale (Kuginuki et al., 1999; Xue et al., 2008), 4-6 weeks after inoculation, where: 0=no galling, 1=a few small galls (small galls on <⅓ of the roots), 2=moderate galling (small to medium-sized galls on ⅓-⅔ of the roots), and 3=severe galling (medium to large-sized galls on >⅔ of the roots). An index of disease (ID) was then calculated according to the formula of Horiuchi and Hori (1980) as modified by Strelkov et al. (2006):

$$ID(\%) = \frac{\sum (n \times 0 + n \times 1 + n \times 2 + n \times 3)}{N \times 3} \times 100\%$$

Where: n is the number of plants in a class; N is the total number of plants in an experimental unit; and 0, 1, 2 and 3 are the symptom severity classes. The ratings 0 and 1 were considered as resistant and 2 and 3 as susceptible phenotypes.

Nine resistant plants were selected and used as DH donors for the CrS clubroot resistance gene (Table 1).

TABLE 1

Screening results on single plants in a growth chamber.

| PLANT | Clubroot (0-3 scale)* | Comments |
| --- | --- | --- |
| CrS-1 | 0 | For DH Donor |
| CrS-2 | 3 | Discarded |
| CrS-3 | 0 | For DH Donor |
| CrS-4 | 0 | For DH Donor |
| CrS-5 | 1 | For DH Donor |
| CrS-6 | 1 | For DH Donor |
| CrS-7 | 1 | For DH Donor |
| CrS-8 | 1 | For DH Donor |
| CrS-9 | 1 | For DH Donor |
| CrS-10 | 0 | For DH Donor |
| CrS-11 | 3 | Discarded |
| CrS-12 | 3 | Discarded |
| CrS-13 | 3 | Discarded |
| CrS-14 | 3 | Discarded |
| CrS-15 | 2 | Discarded |
| CrS-16 | 2 | Discarded |

*Based on a 0-3 rating scale where; 0-1 = R (resistant) and 2-3 = S (susceptible).

The synthetic napus donor has high erucic and high glucosinolate contents that do not meet canola quality standard (which is <2% erucic acid (C22:1) and <30 micromoles total glucosinolates per gram of air-dried oil-free meal), which makes it difficult for commercial breeding to use the source directly. A small DH population derived from the 9 resistant CrS donors was screened for clubroot resistance in a growth chamber with a field mixture and 1 resistant DH plant was selected as a resistant donor. Seed harvested from this plant formed the resistant donor line. Quality data were taken from this seed lot:
  Glucosinolates: 90.41 μmol/g
  C22:1: 11.5%

The selected resistant DH plant was used as a donor for the SOSR crosses. For WOSR, the donor is originating from the same initial segregating synthetic Brassica napus material.

1.1. Resistance Spectrum of the Donors to Different Pathotypes of Clubroot (Plasmodiophora brassicae)

The resistance of the donor line was characterized by differential pathotypes and field isolates from Canada (using the selected resistant DH line described in paragraph 1) and Europe (Germany, France, Netherlands and UK, using plants derived from the initial segregating synthetic Brassica napus material in growth chambers) (Table 2).

TABLE 2

Resistance donor reactions against Canadian and European clubroot pathotypes. Pathotypes for Canada are as classified by Williams (1966) Phytopathology, 56, 624-626; pathotypes for Europe are as classified by Some et al. (1996) Plant Pathology, 45, 432-439.

| Pathotype/Isolate | Region | Donor line | Elite SOSR female breeding line | Elite SOSR male breeding line | Elite WOSR breeding line |
| --- | --- | --- | --- | --- | --- |
| P2 | Canada | R | S | S | NA |
| P3 | Canada | R | S | S | NA |
| P5 | Canada | R | S | S | NA |
| P6 | Canada | R | R | S | NA |
| P8 | Canada | R | S | S | NA |
| Mix pathotypes | Canada | R | S | S | NA |
| P1+ | Europe | R | NA | NA | S |
| P1− | Europe | R | NA | NA | S |
| P2 | Europe | R | NA | NA | S |
| P3− | Europe | R | NA | NA | S |
| P5− | Europe | R | NA | NA | S |
| CR11 (Field isolate) | Europe | R | NA | NA | S |
| CR25 (Field isolate) | Europe | R | NA | NA | S |
| CR30 (Field isolate) | Europe | R | NA | NA | S |
| CR37 (Field isolate) | Europe | R | NA | NA | S |
| CR41 (Field isolate) | Europe | R | NA | NA | S |

2. Mapping Population Development and Molecular Map of a Resistant Loci in the Selected Donor Line From the initial synthetic Brassica napus segregating material described in 1, a resistant plant was crossed with a susceptible WOSR line to produce an F2 mapping population. The F2 population was used to map the resistance locus for CrS. 279 F2 individuals were phenotyped for the resistance against isolate CR11 using growth chamber inoculation method and genotyped.

A single QTL was identified on chromosome A08 (N08) (FIG. 1 and Table 3).

TABLE 3

Markers within the QTL interval for CrS.

| Marker identifier | Chromosome | Pop position (cM) | Significance (−log10(pvalue)) | |
| --- | --- | --- | --- | --- |
| M3 | A08 | 53.144 | 45.89 | Left flanking marker |
| M4 | A08 | 55.486 | 50.42 | |
| M5 | A08 | 55.671 | 50.43 | Peak marker |
| M6 | A08 | 57.137 | 45.45 | Right flanking marker |

Figure 2:
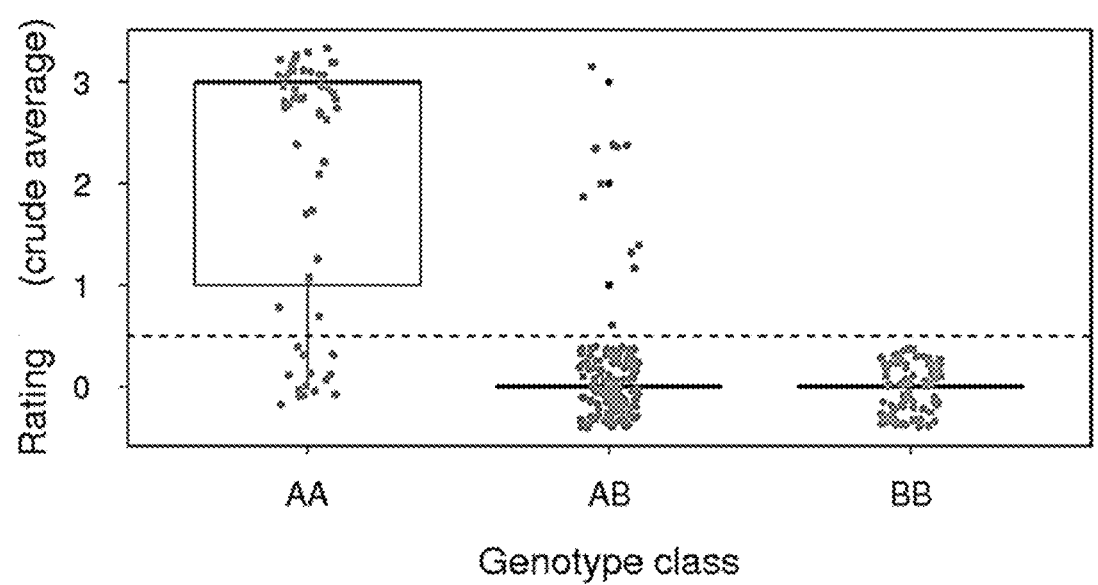
FIG. 2. Resistance rating for lines homozygous for the recurrent parent allele (AA) allele, heterozygous for the recurrent parent and the donor allele (AB), and homozygous for the donor allele (BB) of the peak marker.

At the QTL peak marker, the phenotypic distribution of the F2 plants in the three genotyping classes was analyzed (homozygous with either the recurrent parent (AA) or donor allele (BB), and heterozygous (AB)) (FIG. 2). At the QTL peak marker, heterozygous plants have a similar level of resistance as the homozygous plants for the donor parent allele, showing that the resistance is dominant.

3. Development of Canola Quality and Clubroot Resistant SOSR

Figure 3:
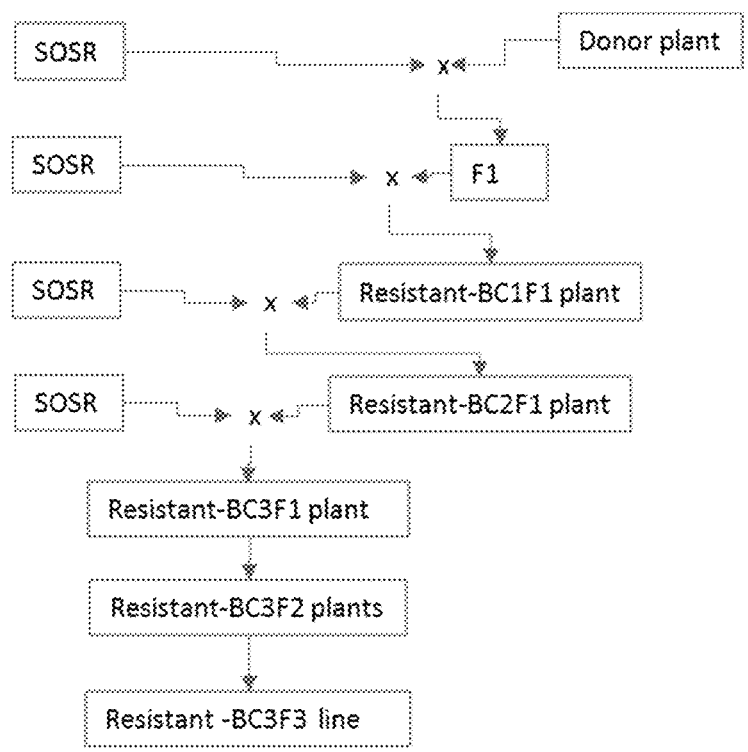
FIG. 3. Backcross scheme to introgress CrS clubroot resistance in a susceptible spring oilseed rape (SOSR) line.

The CrS clubroot resistance was introgressed into SOSR using the DH donor plant described in paragraph 1, following the backcross scheme and combined with phenotypic selection for resistance against a mixture of P3, P5, P6 and P8 in equal portions, as shown in FIG. 3.

A BC3F3 line with resistance against a broad spectrum of different clubroot pathotypes was achieved. The line however has high erucic acid (Table 4), showing that high erucic is linked to CrS clubroot resistance. The levels of glucosinolates were 22.4 μmol/g.

TABLE 4

Resistance of BC3F3 line and levels of erucic acid (%). RP1 is the recurrent parent used in the scheme of FIG. 3 for the BC3F3.

| Phenotype | RP1 | BC3F3 | Susceptible check |
|---|---|---|---|
| P3 | S | R | S |
| P5 | S | R | S |
| P6 | R | R | S |
| P8 | S | R | S |
| Mix pathotypes | S | R | S |
| Erucic (%) | 0 | 12.92 | 0 |

TABLE 5

Field screening of female breeding lines with CrS clubroot resistance. Check: Recurrent parent.

| Rep | Description | Resistance source | Clubroot Rating* (0-3)* | ID** |
|---|---|---|---|---|
| 1 | BC3F3 line | CrS-A08 homozyous | 0 | 0 |
| 2 | BC3F3 line | CrS-A08 homozygous | 0 | 0 |
| 1 | Check (RP) | No CrS | 3 | 100 |
| 2 | Check (RP) | No CrS | 3 | 100 |

*Based on a 0-3 rating scale where; 0-1 = R (resistant) and 2-3 = S (susceptible).
**ID: Index of Disease (%).

TABLE 6

Field screening of hybrid with CrS clubroot resistance at four locations in Alberta.

| HYBRID | CR SOURCE | Location 1 | Location 2 | Location 3 | Location 4 |
|---|---|---|---|---|---|
| Hybrid 1 | No CrS | 99 | 96 | 71 | 82 |
| Hybrid 2 | No CrS | 96 | 96 | 70 | 75 |
| Hybrid 3 | CrS-A08 heterozygous | 0 | 0 | 0 | 0.67 |

**ID = Index of Disease (%). Hybrid 1 and 2: hybrid without CrS. Hybrid 3: result from a cross of BC3F3 with another line without CrS.

BC3F3 breeding lines with the CrS clubroot resistance in homozygous state were grown in a field with natural clubroot infestation (unknown pathotype composition) and screened for resistance. The results are shown in Tables 5 and 6.

Figure 4:
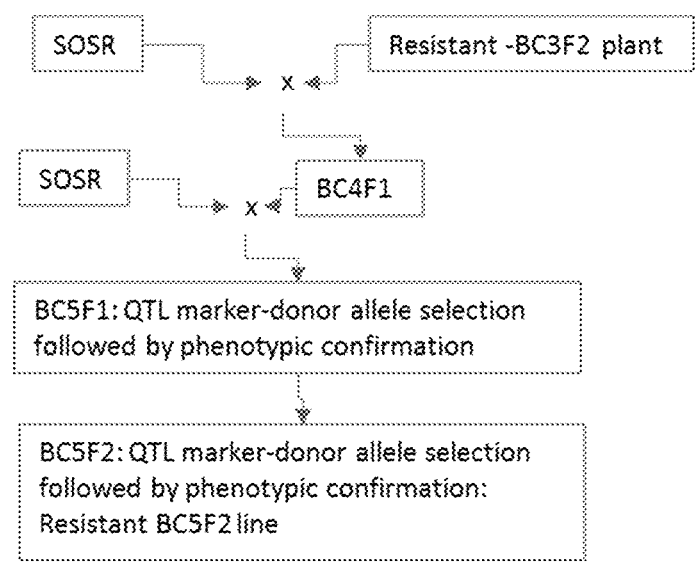
FIG. 4. Selection scheme for canola quality CrS clubroot resistant line. Introgression into a susceptible spring oilseed rape (SOSR) line.

A canola quality line was selected with additional backcrosses (at BC5F2) by removing the high erucic linkage drag using phenotyping for erucic acid, and selecting for the presence of CrS using marker-assisted backcrossing approach and QTL region markers for CrS following the scheme in FIG. 4, and by resistance screening with a mixture of single spore pathotypes including P2, P3, P5, P6 and P8.

To determine the quality parameters, a next generation BC5F3 line was generated from the selected BC5F2 plant. In the BC5F3 line, the level of glucosinolates was 12 µmol/g, and the level of erucic acid was 0.8%. The high erucic acid linkage drag was thus removed in the BC5 generations.

Figure 5:
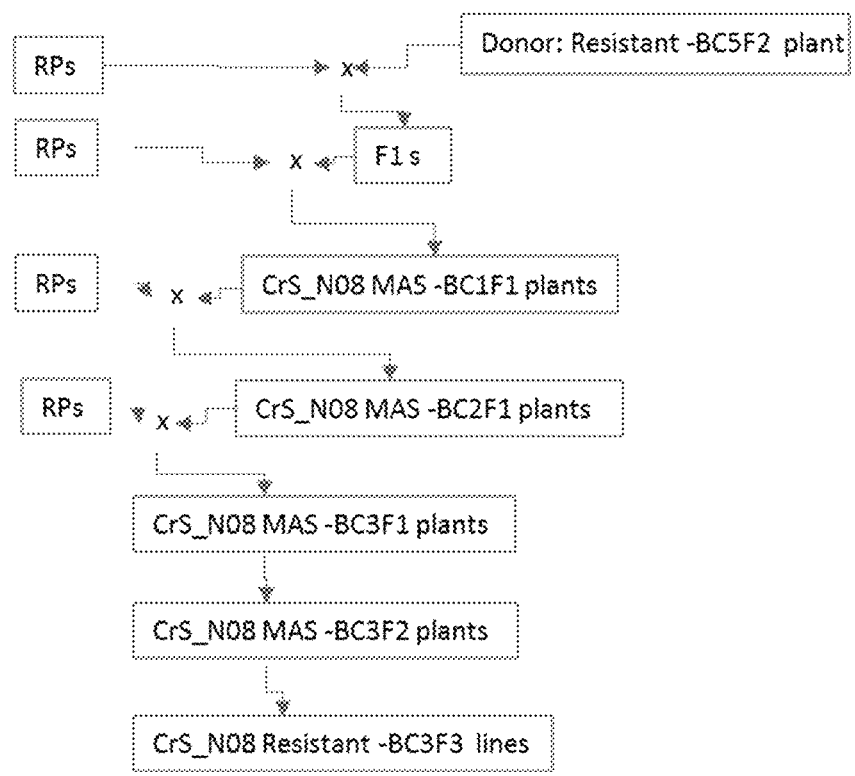
FIG. 5. Marker-assisted backcrossing of CrS clubroot resistance. RP=recurrent parent. MAS: Marker-assisted selection.

The newly created clubroot resistant and canola quality SOSR BC5F2 was then used as donor in trait introgression program for clubroot resistance with marker assisted backcrossing approach (using different recurrent parents) to select resistant lines harbouring a shorter introgression fragment following scheme in FIG. 5. A mixture of single spore pathotypes including P2, P3, P5, P6 and P8 was used for phenotyping the backcross generations.

Six BC3F3 introgression lines were developed using different recurrent parents (IL2 to IL7). The resistance spectrum was determined for the recurrent parents, the donor line (BC5F3 derived from resistant BC5F2 plant) and the introgression lines. Table 7 shows that the donor line shows a broad resistance, and that all introgression lines show the same spectrum of resistance as the donor line. Further, one BC3F2 plant from introgression line IL4 was selected (IL4 BC3F2). This line was derived from a different individual than the IL4 BC3F3 plant. The IL4 BC3F2 plant has the same resistance spectrum as the IL4 BC3F3 plant.

Markers were used to identify the chromosomal region required for CrS clubroot resistance. IL4 BC3F3 contained the minimum number of CrS markers at the left side, delimiting the chromosomal region required for CrS clubroot resistance at the left side. IL4 BC3F2 contained the minimum number of CrS markers at the right side, delimiting the chromosomal region required for CrsS clubroot resistance at the right side. Marker data for the BC5F2 donor plant (indicated as IL1 in Table 8) and for the introgression lines are shown in Table 8.

TABLE 7

Resistance spectrum of canola-quality donor BC5F3 line and different introgression BC3F3 lines (IL), and the susceptible Recurrent Parent (RP1). Mix: mixture of single spore pathotypes including P2, P3, P5, P6 and P8. Isolates 1-10: field populations each obtained from a single club from different plants. Isolate 1 corresponds to 5X, isolate 5 to 8P, 6 to 2B, and 7 to 3A of the Canadian Clubroot Differential Set (CCD) (Strelkov et al., 2018, Can J Plant Pathology pp 284).

| Pathotype/Isolate | Donor BC5F3 | RP1 | IL2 | RP2 | IL3 | RP3 | IL4 | RP4 | IL5 | RP5 | IL6 | RP6 | IL7 | RP7 |
|---|---|---|---|---|---|---|---|---|---|---|---|---|---|---|
| P2 | R | S | R | S | R | S | R | S | R | S | R | S | R | S |
| P3 | R | S | R | S | R | S | R | S | R | S | R | S | R | S |
| P5 | R | S | R | S | R | S | R | S | R | S | R | S | R | S |
| P6 | R | R | R | R | R | R | R | R | R | S | R | S | R | S |
| P8 | R | S | R | S | R | S | R | S | R | S | R | S | R | S |
| Mix | R | S | R | S | R | S | R | S | R | S | R | S | R | S |
| Isolate 1 (5X) | R | S | R | S | R | S | R | S | R | S | R | S | R | S |
| Isolate 2 | R | S | R | S | R | S | R | S | R | S | R | S | R | S |
| Isolate 3 | R | S | R | S | R | S | R | S | R | S | R | S | R | S |
| Isolate 4 | S | S | S | S | S | S | S | S | S | S | S | S | S | S |
| Isolate 5 (8P) | R | S | R | S | R | S | R | S | R | S | R | S | R | S |
| Isolate 6 (2B) | R | S | R | S | R | S | R | S | R | S | R | S | R | S |
| Isolate 7 (3A) | R | S | R | S | R | S | R | S | R | S | R | S | R | S |
| Isolate 8 | R | S | R | S | R | S | R | S | R | S | R | S | R | S |

TABLE 7-continued

Resistance spectrum of canola-quality donor BC5F3 line and different introgression BC3F3 lines (IL), and the susceptible Recurrent Parent (RP1). Mix: mixture of single spore pathotypes including P2, P3, P5, P6 and P8. Isolates 1-10: field populations each obtained from a single club from different plants. Isolate 1 corresponds to 5X, isolate 5 to 8P, 6 to 2B, and 7 to 3A of the Canadian Clubroot Differential Set (CCD) (Strelkov et al., 2018, Can J Plant Pathology pp 284).

| Pathotype/Isolate | Donor BC5F3 | RP1 | IL2 | RP2 | IL3 | RP3 | IL4 | RP4 | IL5 | RP5 | IL6 | RP6 | IL7 | RP7 |
|---|---|---|---|---|---|---|---|---|---|---|---|---|---|---|
| Isolate 9 | R | S | R | S | R | S | R | S | R | S | R | S | R | S |
| Isolate 10 | R | S | R | S | R | S | R | S | R | S | R | S | R | S |

4. Development of Canola Quality and Clubroot Resistant WOSR

Figure 6:
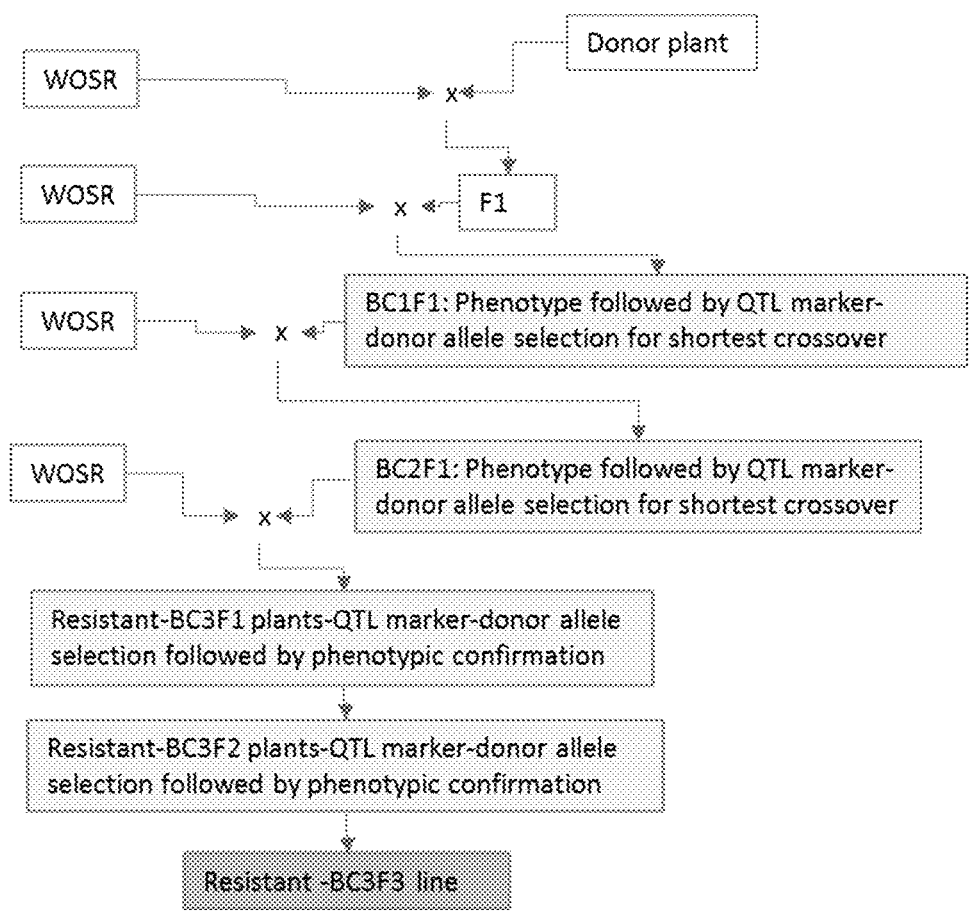
FIG. 6. Introgression scheme of CrS clubroot resistance into susceptible winter oilseed rape (WOSR).

The CrS resistance locus was also introgressed into a WOSR elite breeding line with the scheme as shown in FIG. 6. As stated before, the donor plant is originating from the same initial segregating *Brassica napus* material as for the donor used in the SOSR crossing schemes. Phenotypic selection was performed using *Plasmodiophora brassicae* isolate CR11 in combination with marker-donor allele selection.

In the BC1F1 generation, lines with low levels of erucic acid were obtained.

Marker data for the BC1F1 introgression line (clubroot resistant, low erucic acid content) and for the BC2F1 introgression line (clubroot resistant, low erucic acid content) are shown in Table 8.

5. Position of the CrS Resistance Locus with Low Erucic Acid on Chromosome A08

The markers used for introgression of the clubroot resistance locus in WOSR and SOSR are shown in Table 8. For each marker, the position on the public genome reference of Darmor-bzh (version 8.1, Bayer et al., 2017, Plant Biotech J. 15, p. 1602) and the genetic position on the F2 WOSR genetic map (described in paragraph 2) are provided. Considering the marker order based on their genetic position on the F2 genetic map, Table 8 displays that at the left side of the resistance locus, the markers M1 to M3 are not required for resistance (see, IL4 for the closest marker M3) and that at the right side, the markers M6-M11 are not required for resistance (see, IL4 BC3F2 for closest marker M6). This shows that the marker interval between marker M3 and marker M6 (or, the marker interval from marker M4 to marker M5) is sufficient for CrS clubroot resistance based on the F2 genetic map.

When comparing the marker order from the F2 WOSR genetic map with the order on the genome reference of Darmor-bzh (v 8.1), there appears a discrepancy for marker M9. For presenting all genotyping information from the different backcrosses in WOSR and SOSR in Table 8, we have presented the marker order following the genetic position on the F2 WOSR genetic map (which was constructed using the same initial parents as for the WOSR BC1F1 and BC2F1).

Moreover, Table 8 shows that a fragment as long as the fragment from marker M4 to marker M11 based on the F2 genetic map can be used to obtain clubroot resistance while not introducing high erucic acid.

The plants converted to the RP on the left side of marker M4 (using the genetic position of the markers in the F2 population) were having low erucic acid levels in the seeds. At the right side, marker M11 is at the end of the chromosome, and the region that confers high erucic can thus not be located at the right side of M11. This shows that the region in the donor that confers high erucic acid is located at the left side of marker M4. In order to obtain plants with low erucic acid, the region at the left side of marker M4 should be derived from the RP. As FAE1 is a key gene in the biosynthesis of erucic acid in oilseed rape, its position on the genome of Darmor-bzh was checked using the accession number EU543282 as a blast query and the public structural annotation of the genome (Bayer et al, supra) for identifying the gene position. One copy of the gene is located on chromosome A08 (that would correspond to BnaA08g11590D2—position 11,261,862 bp to 11,263,382 bp on the genome of Darmor-bzh).

*Brassica* seeds comprising the CrS clubroot resistance locus and low levels of erucic acid have been deposited at the NCIMB (NCIMB Ltd, Ferguson Building, Craibstone Estate, Bucksburn, Aberdeen AB21 9YA, Scotland, UK) on Jan. 21, 2019, under accession number NCIMB 43341.

TABLE 8

Marker data of resistant donor lines, susceptible recurrent parent, and resistant and low erucic introgression lines. Annotation: marker allele is from the susceptible recurrent parent (RP, RP4 or non CrS) or from the resistant donor line (CrS). "—" was indicated in case the assay was not run. N.i. is non-informative. Genotypes indicated with an asterisk: not determined in the respective line itself, but inferred from data on another generation.

| gene identifier (from the structural annotation in Bayer et al. 2017) | marker identifier | chromosome Darmor-bzh genome (v8.1) | position Darmor-bzh genome (V8.1), in bp | chromosome genetic map (F2 map) | genetic map position (F2 map), in cM | Recurrent parent (RP, susceptible | Donor parent (resistant, high erucic) | WOSR Donor parent (resistant, BC1F1 (resistant, low erucic) | Annotation BC1F1 | BC2F1 (resistant, low erucic) | Annotation BC2F1 |
|---|---|---|---|---|---|---|---|---|---|---|---|
|  | M1 | A08 | 13,108,209 | A08 | 48.66 | CC | TT | CC | RP | CC* |  |
|  | M2 | A08 | 12,499,060 | A08 | 51.99 | GG | AA | GG | RP | GG* |  |
| BnaA08g11590D2 |  | A08 | 11,261,862-11,263,382 |  |  |  |  |  |  |  |  |
|  | M3 | A08 | 11,256,444 | A08 | 53.14 | GG | AA | No call | — | — |  |
| BnaA08g11690D2 |  | A08 | 10,531,290-10,532,568 |  |  |  |  |  |  |  |  |
|  | M4 | A08 | 10,369,430 | A08 | 55.49 | CC | AA | AC | CrS | AC | CrS |
|  | M5 | A08 | 10,375,744 | A08 | 55.67 | CC | TT | No call |  | — |  |
|  | M6 | A08 | 9,801,311 | A08 | 57.14 | AA | GG | AG | CrS | AG | CrS |
|  | M7 | A08 | 9,699,466 | A08 | 57.50 | CC | TT | TC | CrS | TC | CrS |
|  | M8 |  |  | A08 | 58.77 | TT | CC | — |  | — |  |
|  | M9 |  |  | A08 | 59.14 | CC | TT | — |  | — |  |
|  | M10 | A08 | 11,933,021 | A08 | 59.32 | GG | AA | AG | CrS | GG | RP |
|  | M11 | A08 | 933,572 | A08 | 66.98 | GG | AA | AG | CrS | GG | RP |

TABLE 8-continued

Marker data of resistant donor lines, susceptible recurrent parent, and resistant and low erucic introgression lines. Annotation: marker allele is from the susceptible recurrent parent (RP, RP4 or non CrS) or from the resistant donor line (CrS). "—" was indicated in case the assay was not run. N.i. is non-informative. Genotypes indicated with an asterisk: not determined in the respective line itself, but inferred from data on another generation.

| gene identifier (from the structural annotation in Bayer et al. 2017) | marker identifier | Recurrent parent (susceptible) | Donor parent (resistant, high erucic) | IL1 (BC5F2, resistant, low erucic) | Annotation IL1 | SOSR Recurrent parent 4 (RP4, susceptible) | IL4 (BC3F3, resistant, low erucic) | Annotation IL4 BC3F3 | IL4 (BC3F2, resistant, low erucic) | Annotation IL4 BC3F2 |
|---|---|---|---|---|---|---|---|---|---|---|
| BnaA08g11590D2 | M1 | CC | TT | CC | RP | CC | CC | Non CrS | — | n.i. |
|  | M2 | AA | AA | AA | n.i. | GG | AA | n.i. | AG | n.i. |
| BnaA08g10690D2 | M3 | GG | AA | GG | RP | GG | GG | Non CrS | — |  |
|  | M4 | CC | AA | AA | CrS | CC | AA | CrS | AC | CrS |
|  | M5 | CC | TT | TT | CrS | CC | TT | CrS | — |  |
|  | M6 | AA | GG | GG | CrS | AA | GG | CrS | AA | RP4 |
|  | M7 | CC | TT | TT | CrS | CC | TT | CrS | CC | RP4 |
|  | M8 | TT | CC | CC | CrS | TT | CC | CrS | — |  |
|  | M9 | CC | TT | TT | CrS | CC | CC | CrS | — |  |
|  | M10 | GG | AA | AA | CrS | GG | GG | RP4 | GG | RP4 |
|  | M11 | GG | AA | AA | CrS | GG | GG | RP4 | — |  |

TABLE 9

Identity of the markers.

| Marker ID | 5' flanking sequence | Polymorphic base in resistant source | Polymorphic base in susceptible line | 3' flanking sequence |
|---|---|---|---|---|
| M1 | SEQ ID NO: 1 | T | C | SEQ ID NO: 2 |
| M2 | SEQ ID NO: 3 | A | G | SEQ ID NO: 4 |
| M3 | SEQ ID NO: 5 | A | G | SEQ ID NO: 6 |
| M4 | SEQ ID NO: 7 | A | C | SEQ ID NO: 8 |
| M5 | SEQ ID NO: 9 | T | C | SEQ ID NO: 10 |
| M6 | SEQ ID NO: 11 | G | A | SEQ ID NO: 12 |
| M7 | SEQ ID NO: 13 | T | C | SEQ ID NO: 14 |
| M8 | SEQ ID NO: 15 | C | T | SEQ ID NO: 16 |
| M9 | SEQ ID NO: 17 | T | C | SEQ ID NO: 18 |
| M10 | SEQ ID NO: 19 | A | G | SEQ ID NO: 20 |
| M11 | SEQ ID NO: 21 | A | G | SEQ ID NO: 22 |

6. Validation of the CRR1a Clubroot Resistance Gene in a Transgenic Approach

A blast analysis was performed to identify the position of the CRR1a clubroot resistance gene (as described by Hatakeyama et al (2013) PLos One 8(1) e54745; accession number AB605024) on the public genome of Darmor-bzh (version 8.1). Using the public structural annotation of the genome (Bayer et al., supra), the gene would correspond to the BnaA08g10690D2 gene, localized from 10,531,290 to 10,532,568 bp on chromosome A08. This corresponds to the marker interval between marker M3 and marker M4, taking into account the position of those two markers on the Darmor-bzh genome (see Table 8).

The CRR1a gene (as described by Hatakeyama et al (2013) PLos One 8(1) e54745; accession number AB605024) was cloned under control of the constitutive 35S promoter and transformed into susceptible *Brassica napus* plants. The plants were challenged against *Plasmodiophora brassicae* isolate CR6 in greenhouse conditions. A total of 4 transgenic lines and their respective segregating lines were evaluated for clubroot resistance.

The inoculum was prepared using clubbed roots from symptomatic plants from a previous experiment that were stored at −20° C. Symptomatic roots were homogenized by using a Polytron in 40 ml of distilled water. The resulting homogenate was passed through a Miracloth an afterwards, centrifuged (2000 g for 10 minutes) to remove as much plant debris as possible. The resulting supernatant was passed to a new 50 ml tube and resting structures were checked in the microscope. Small spherical spores were observed confirming the presence of *P. brassicae* in the inoculum. Ten days-old transgenic plants were inoculated by root dipping using the obtained spore suspension or distilled water (mock inoculations). After 10 minutes of root dip, plants were transferred to soil and maintained in separated trays. Plant symptoms were evaluated at 60 days post-inoculation (dpi). Two resistant breeding lines were included as controls. None of the mock inoculated plants showed root symptoms after 60 dpi. As expected, no symptoms and clubbed roots were obtained for the two control breeding lines.

The transgenic lines with the CRR1a gene showed symptomatic clubbed roots.

These data show that the CRR1a gene is not sufficient for clubroot resistance to isolate CR6.

---

The invention claimed is:

1. A *Brassica* plant comprising <2% erucic acid in the seed oil, and comprising a CrS clubroot resistance locus in a chromosomal segment comprising the marker interval from marker M4 to marker M5,
    wherein the marker M4 comprises a 5' flanking sequence of SEQ ID NO: 7, a polymorphic base, and a 3' flanking sequence of SEQ ID NO: 8, wherein the polymorphic base is A, and
    wherein the marker M5 comprises a 5' flanking sequence of SEQ ID NO: 9, a polymorphic base, and a 3' flanking sequence of SEQ ID NO: 10, wherein the polymorphic base is T.

2. The *Brassica* plant according to claim 1, which is a *Brassica napus* or a *Brassica rapa* plant.

3. The *Brassica* plant according to claim 2, which is a *Brassica napus* WOSR plant or a *Brassica napus* SOSR plant.

4. The *Brassica* plant according to claim 1, wherein said chromosomal segment is obtainable from reference seeds deposited at NCIMB under accession number NCIMB 43341.

5. The Brassica plant according to claim 1, which is resistant to *P. brassicae* pathotypes P2, P3, P5, P6 or P8 or to isolate CR11.

6. The *Brassica* plant according to claim 1, wherein said plant is heterozygous for said clubroot resistance locus.

7. The *Brassica* plant according to claim 1, wherein said plant is homozygous for said clubroot resistance locus.

8. The *Brassica* plant according to claim 1, said plant further comprising a gene conferring herbicide tolerance.

9. The Brassica plant according to claim 8, wherein said gene conferring herbicide tolerance is a gene which confers resistance to glufosinate or to glufosinate ammonium or a gene conferring resistance to glyphosate.

10. Seeds of the Brassica plants according to claim 1, wherein said seeds comprise a CrS clubroot resistance locus in a chromosomal segment comprising the marker interval from marker M4 to marker M5, and comprise <2% erucic acid in the seed oil,
    wherein the marker M4 comprises a 5' flanking sequence of SEQ ID NO: 7, a polymorphic base, and a 3' flanking sequence of SEQ ID NO: 8, wherein the polymorphic base is A, and
    wherein the marker M5 comprises a 5' flanking sequence of SEQ ID NO: 9, a polymorphic base, and a 3' flanking sequence of SEQ ID NO: 10, wherein the polymorphic base is T.

11. A method for producing a clubroot resistant *Brassica* plant, said method comprising
    (a) identifying at least one *Brassica* plant comprising a CrS clubroot resistance locus in a chromosomal segment comprising the marker interval from M4 to M5, and
    (b) selecting a plant comprising said CrS clubroot resistance locus,
    wherein the marker M4 comprises a 5' flanking sequence of SEQ ID NO: 7, a polymorphic base, and a 3' flanking sequence of SEQ ID NO: 8, wherein the polymorphic base is A, and
    wherein the marker M5 comprises a 5' flanking sequence of SEQ ID NO: 9, a polymorphic base, and a 3' flanking sequence of SEQ ID NO: 10, wherein the polymorphic base is T.

12. A method for producing a clubroot resistant *Brassica* plant, said method comprising
    (a) crossing a first *Brassica* plant comprising a CrS clubroot resistance locus in a chromosomal segment comprising the marker interval from M4 to M5 with a second plant; and
    (b) identifying a progeny plant comprising the marker interval from M4 to M5; or
    comprising introducing the CrS clubroot resistance locus into a plant not comprising the CrS clubroot resistance locus using genome editing,
    wherein the marker M4 comprises a 5' flanking sequence of SEQ ID NO: 7, a polymorphic base, and a 3' flanking sequence of SEQ ID NO: 8, wherein the polymorphic base is A, and
    wherein the marker M5 comprises a 5' flanking sequence of SEQ ID NO: 9, a polymorphic base, and a 3' flanking sequence of SEQ ID NO: 10, wherein the polymorphic base is T.

13. A method for the protection of a group of cultivated plants according to claim 8 in a field comprising applying a composition comprising one or more herbicidal active ingredients.

14. The method according to claim 13, wherein the herbicide is glufosinate or glufosinate ammonium or glyphosate.

* * * * *

SEQUENCE LISTING

<160> NUMBER OF SEQ ID NOS: 22

<210> SEQ ID NO 1
<211> LENGTH: 60
<212> TYPE: DNA
<213> ORGANISM: Brassica napus

<400> SEQUENCE: 1
gtgaggcaaa tagacaaacc ccacatacta catttatgca ttttcctata cagcaagata    60

<210> SEQ ID NO 2
<211> LENGTH: 60
<212> TYPE: DNA
<213> ORGANISM: Brassica napus

<400> SEQUENCE: 2
atcakatatg tagcatagtt gaaaaagcaa agaagacgtc atacataacr tatgattcat    60

<210> SEQ ID NO 3
<211> LENGTH: 150
<212> TYPE: DNA
<213> ORGANISM: Brassica napus

<400> SEQUENCE: 3
ctttagttgt aacaacaaaa acatatcgat aagatgtaga attgaccatg cctaataata    60
ttacattatt attcatcaac attgagaaca tacatcaaga gaaacatggt tgtgttcagg   120
aatctcttcc ttctttctaa tgttaacctt                                    150

<210> SEQ ID NO 4
<211> LENGTH: 150
<212> TYPE: DNA
<213> ORGANISM: Brassica napus

<400> SEQUENCE: 4
cccaaaacaa gtctcgccca ctcaccaaaa tatgtctcat tgtatccaat catagcgttt    60
ttataaacca acgacataca tcgcttatca gtatcaggaa acttacatgt ttctccaaag   120
gggtcatgcc acgctccttc atgtctcatc                                    150

<210> SEQ ID NO 5
<211> LENGTH: 60
<212> TYPE: DNA
<213> ORGANISM: Brassica napus

<400> SEQUENCE: 5
ttctactgca gtgtagaata tagagggatg ttaccatttt atycatttat attttcttct    60

<210> SEQ ID NO 6
<211> LENGTH: 60
<212> TYPE: DNA
<213> ORGANISM: Brassica napus

<400> SEQUENCE: 6
ttataaagac ataccactac aacaaatcta caataaaatt gctctattct aaaaaacaat    60

<210> SEQ ID NO 7
<211> LENGTH: 60
<212> TYPE: DNA
<213> ORGANISM: Brassica napus

<400> SEQUENCE: 7
agtatrccgg cggaactctt ttttgtgtgt tgcaagtacg acgcaacaag tgagagaaca    60

<210> SEQ ID NO 8
<211> LENGTH: 60
<212> TYPE: DNA
<213> ORGANISM: Brassica napus

<400> SEQUENCE: 8
agaagaaaag aatcaaactt gtcattarca aayaacatta saastttaa tmatcaaaac    60

<210> SEQ ID NO 9
<211> LENGTH: 18
<212> TYPE: DNA
<213> ORGANISM: Brassica napus

```
<400> SEQUENCE: 9
aatagtaagt tccccttc                                                18

<210> SEQ ID NO 10
<211> LENGTH: 77
<212> TYPE: DNA
<213> ORGANISM: Brassica napus

<400> SEQUENCE: 10
ctagcaatcg ctaagctgtg cccatggaag agaagaagaa ccaaatttca acacaacata    60
ctttagcccc aaaggaa                                                   77

<210> SEQ ID NO 11
<211> LENGTH: 60
<212> TYPE: DNA
<213> ORGANISM: Brassica napus

<400> SEQUENCE: 11
tatttataaa aaaaaattga ggtccggatg tgcctagaac cggccttgct agtattgtta    60

<210> SEQ ID NO 12
<211> LENGTH: 60
<212> TYPE: DNA
<213> ORGANISM: Brassica napus

<400> SEQUENCE: 12
atgataaaga aaattttatt accaaactca gtccatggaa taaggcatct tgagcaatga    60

<210> SEQ ID NO 13
<211> LENGTH: 60
<212> TYPE: DNA
<213> ORGANISM: Brassica napus

<400> SEQUENCE: 13
actctcatat gctcttttta aattggaatt aaatcctctg aataaggaca ccacaaatac    60

<210> SEQ ID NO 14
<211> LENGTH: 60
<212> TYPE: DNA
<213> ORGANISM: Brassica napus

<400> SEQUENCE: 14
yaaaatatca tatcaataat agtgattgat tccatraaat ttcttgataa tttatgttgt    60

<210> SEQ ID NO 15
<211> LENGTH: 150
<212> TYPE: DNA
<213> ORGANISM: Brassica napus

<400> SEQUENCE: 15
aattacacca cctgcaatat ccgcaaggac aggtatatrt tttsgatgag tgcacatyct    60
tttattccac gaatctagaa aaggaaaagc attggtcgtc ccaagatcaa gaccggtaaa   120
acttagtcat aagtttatag taactgcatt                                    150

<210> SEQ ID NO 16
<211> LENGTH: 150
<212> TYPE: DNA
<213> ORGANISM: Brassica napus

<400> SEQUENCE: 16
tttaacagat tattgattmt atcgtggaaa cacrcctaat atgtatcttt twaataaacc    60
```

```
wttctaaawa atcagaagaa acttcttgct gctacatkat catayacact cacctgtggg    120
gtgtgaaaca ggagtcgcar ctgtcwtaat                                    150
```

<210> SEQ ID NO 17
<211> LENGTH: 60
<212> TYPE: DNA
<213> ORGANISM: Brassica napus

<400> SEQUENCE: 17

```
aggaagataa cgatgatcta ttgtcgtaag gattgtgtag gattgtagtt gcagtgattt    60
```

<210> SEQ ID NO 18
<211> LENGTH: 60
<212> TYPE: DNA
<213> ORGANISM: Brassica napus

<400> SEQUENCE: 18

```
gaaattgtgg aagaagaaga agaagyagag ggmgtttgac ttccaytytc ttcatttcaa    60
```

<210> SEQ ID NO 19
<211> LENGTH: 60
<212> TYPE: DNA
<213> ORGANISM: Brassica napus

<400> SEQUENCE: 19

```
ccccggttcc ttgaaagatt gctttcgctg aagctagaag tttgtgtccc tgttccagta    60
```

<210> SEQ ID NO 20
<211> LENGTH: 60
<212> TYPE: DNA
<213> ORGANISM: Brassica napus

<400> SEQUENCE: 20

```
cttccctgaa taccaatcca tgaaaaactt tccatatwta twtatactgt tccatgttcc    60
```

<210> SEQ ID NO 21
<211> LENGTH: 60
<212> TYPE: DNA
<213> ORGANISM: Brassica napus

<400> SEQUENCE: 21

```
agcccaatgt tagatgggtt ctttctgact catacttgga tgttaagaac aaagactatg    60
```

<210> SEQ ID NO 22
<211> LENGTH: 60
<212> TYPE: DNA
<213> ORGANISM: Brassica napus

<400> SEQUENCE: 22

```
aggtaagtcg atttgctctg acagttgtgt gcaatgtagt aacaacatct cttataagrg    60
```